US006174682B1

(12) United States Patent
Khodadoust

(10) Patent No.: US 6,174,682 B1
(45) Date of Patent: Jan. 16, 2001

(54) THIOREDOXIN FAMILY ACTIVE SITE MOLECULES AND USES THEREFOR

(75) Inventor: Mehran M. Khodadoust, Chestnut Hill, MA (US)

(73) Assignee: Millenium Pharmaceuticals, Inc., Cambridge, MA (US)

( * ) Notice: Under 35 U.S.C. 154(b), the term of this patent shall be extended for 0 days.

(21) Appl. No.: 09/264,419

(22) Filed: Mar. 8, 1999

(51) Int. Cl.[7] .............................. C12Q 1/68; C12N 9/02; C12N 1/20; C12N 15/00; C07M 21/04

(52) U.S. Cl. .......................... 435/6; 435/189; 435/252.3; 435/320.1; 435/810; 536/23.2; 536/23.4; 536/23.5

(58) Field of Search ........................... 435/6, 189, 252.3, 435/320.1, 810; 536/23.2, 23.4, 23.5

(56) References Cited

FOREIGN PATENT DOCUMENTS

WO 99/14328   3/1999   (WO) .
WO 99/38881   8/1999   (WO) .

OTHER PUBLICATIONS

Eklund, H. et al., "Structural and Functional Relations Among Thioredoxins of Different Species", *Proteins*, 11(1):13–28 (1991).
Wong, J. et al., "Cloning of a cDNA encoding an *Acanthamoeba castellanii* PDI–like protein" *Gene*, 150(1):175–9 (1994).
Hayano, T. et al., "Protein disulfide isomerase mutant lacking its isomerase activity accelerates protein folding in the cell" *FEBS Lett*, 377(3):505–11 (1995).
Robinson, A. et al., "Constitutive overexpression of secreted heterologous proteins decreases extractable BiP and protein disulfide isomerase levels in *Saccharomyces cerevisiae*" *Biotechnol Prog*, 11(2):171–7 (1995).
Kivirikko, K. et al., "Prolyl 4–hydroxylases and their protein disulfide isomerase subunit" *Matrix Biol*, 16(7):357–68, (1998).
Freedman, R. et al., "Protein disulphide isomerase: building bridges in protein folding" *Trends Biochem Sci*, 19(8):331–6 (1994).
Gleason, K et al., "Thioredoxin and related proteins in procaryotes" *FEMS Microbiol Rev*. 4(4):271–97 (1988).
Kivirikko, K.I. et al., "Collagen Hydroxylases and the protein Disulfide Isomerase Subunit of Prolyl 4–Hydroxylases" Adv. Enzymol. Related Areas Mol. Biol. 72:325–380 (1998).
Baksh, S. et al., "Interaction of calreticulin with protein disulfude isomerase", *J. Biol Chem*. 270(52):31338–44 (1995).

Vuorela, A. et al., "Assembly of human prolyl 4–hydroxylase and type III collagen in the yeast pichia pastoris: formation of a stable enzyme tetramer requires coexpression with collagen and assembly of a stable collagen requires coexpression with prolyl 4–hydroxylase", *EMBO J.* 16(22):6702–12 (1997).
Laboissiere, M. et al., "The essential function of protein–disulfide isomerase is to unscramble non–native disulfide bonds", *J Biol Chem*. 270(47):28006–9 (1995).
Holst, B., et al. "Active site mutations in yeast protein disulfide isomerase cause dithiothreitol sensitivity and a reduced rate of protein folding in the endoplasmic reticulum" *J Cell Biol*. 138(6):1229–38 (1997).
Adams, "Initial assessment of human gene diversity and expression patterns based upon 83 million nucleotides of cDNA sequence," 1995, *Nature*, 377:3–174.
Albrecht, J.C. et al., "Primary structure of the herpesvirus saimiri genome," 1992, *J. Virol.*, 66(8):5047–5058.
Andersson, B. et al., "A "double adaptor" method for improved shotgun library construction," 1996, *Anal. Biochem.*, 236(1):107–113.
Chaudhuri, M.M. et al., "The gene for a novel protein, a member of the protein disulphide isomerase/form I phosphoinositide–specific phospholipase C family, is amplified in hydroxyurea–resistant cells," 1992, *Biochem j.*, 281:645–650.
GenBank™ Accession No. AA356777 for EST65381 Jurkat T–cells III *Homo sapiens* cDNA 5'0 end similar to similar to *S. cerevisiae* hypothetical protein (GB:Z36103) YBR234c.
GenBank™ Accession No. AA356577 for EST65145 Jurkat T–cells VI *Homo sapiens* cDNA 5' end similar to similar to phospholipase C, alpha.
GenBank™ Accession No. AA356542 for EST65106 Jurkat T–cells VI *Homo sapiens* cDNA 5'0 end similar to similar to protein disulfide isomerase P5, mRNA sequence.
GenBank™ Accession No. AA353906 for EST62094 Jurkat T–cells V *Homo sapiens* cDNA 5'0 end.
GenBank™ Accession No. AA356578 for EST65146 Jurkat T–cells VI *Homo sapiens* cDNA 5'0 end similar to similar to thiol protease family.

(List continued on next page.)

Primary Examiner—Elizabeth Slobodyansky
(74) Attorney, Agent, or Firm—Lahive & Cockfield, LLP; Amy E. Mandragouras, Esq.

(57) ABSTRACT

Novel thioredoxin family active site molecules, designated MP-4 polypeptides, proteins, and nucleic acid molecules, are disclosed. In addition to isolated, full-length MP-4 proteins, the invention further provides isolated MP-4 fusion proteins, antigenic peptides and anti-MP-4 antibodies. The invention also provides MP-4 nucleic acid molecules, recombinant expression vectors containing a nucleic acid molecule of the invention, host cells into which the expression vectors have been introduced and non-human transgenic animals in which a MP-4 gene has been introduced or disrupted. Diagnostic, screening and therapeutic methods utilizing compositions of the invention are also provided.

48 Claims, 4 Drawing Sheets

OTHER PUBLICATIONS

GenBank™ Accession No. AA913737 for o138h07.s1 Soares_NFL_T_GBC_S1 *Homo sapiens* cDNA clone IMAGE:1525789 3'.

GenBank™ Accession No. R34190 for yh84d03.r1 Soares placenta Nb2HP *Homo sapiens* cDNA clone IMAGE:136421 5'.

GenBank™ Accession No. AA732423 for nz92c10.s1 NCI_CGAP_GCB1 *Homo sapiens* cDNA clone IMAGE:1302930 3'.

GenBank™ Accession No. AA318503 for EST20585 Spleen I *Homo sapiens* cDNA 5' end similar to similar to protein disulfide isomerase P5.

GenBank™ Accession No. T72824 for yc51f07.r1 Stratagene liver (#937224) *Homo sapiens* cDNA clone IMAGE:84229 5'.

GenBank™ Accession No. R79616 for yi88g10.r1 Soares placenta Nb2HP *Homo sapiens* cDNA clone IMAGE:146370 5'.

GenBank™ Accession No. AA471271 for PMY2348 KG1–a Lambda Zap Express cDNA library *Homo sapiens* cDNA 5'.

GenBank™ Accession No. AQ266302 for RPCI11–72N3.TJ RPCI–11 *Homo sapiens* genomic clone RPCI–11–72N3, genomic survey sequence.

GenBank™ Accession No. AA458144 for vg46b09.r1 Soares mouse mammary gland NbMMG *Mus musculus* cDNA clone IMAGE:864377 5', mRNA sequence.

GenBank™ Accession No. AA125098 for mp77e01.r1 Soares 2NbMT *Mus musculus* cDNA clone IMAGE:575256 5', mRNA sequence.

GenBank™ Accession No. AA204354 for mt49g02.r1 Stratagene mouse embryonic carcinoma (#937317) *Mus musculus* cDNA clone IMAGE:633266 5' similar to TR:G456013 G456013 Disulfide–Like Protein. ;, mRNA sequence.

GenBank™ Accession No. AA631495 for np83h01.s1 NCI_CGAP_Thy1 *Homo sapiens* cDNA clone IMAGE:1132945, mRNA sequence.

GenBank™ Accession No. X96770 for *S. cerevisiae* chromosome XVI, left arm DNA.

GenBank™ Accession No. C89225 for C89225 Mouse early blastocyst cDNA *Mus musculus* cDNA clone 01B00060IF11, mRNA sequence.

GenBank™ Accession No. AA670112 for ab55a08.s1 Stratagene lung carcinoma 937218 *Homo sapiens* cDNA clone IMAGE:844694 3', mRNA sequence.

GenBank™ Accession No. Z73514 for *S.cerevisiae* chromosome XVI reading frame ORF YPL158c.

GenBank™ Accession No. D63874 for Human mRNA for HMG–1, complete cds.

GenBank™ Accession No. AA869069 for vq30d04.r1 Barstead stromal cell line MPLRB8 *Mus musculus* cDNA clone IMAGE:1095751 5', mRNA sequence.

GenBank™ Accession No. U51677 for Human non–histone chromatin protein HMG1 (HMG1) gene, complete cds.

GenBank™ Accession No. D32209 for Rat mRNA for leucine–rich acidic nuclear protein, complete cds.

GenBank™ Accession No. AF043907 for *Hydra magnipapillata* spinalin mRNA, complete cds.

GenBank™ Accession No. X12597 for Human mRNA for high mobility group–1 protein (HMG–1).

GenBank™ Accession No. AE001403 for *Plasmodium falciparum* chromosome 2, section 40 of 73 of the complete sequence.

GenBank™ Accession No. AA206943 for zq83a01.r1 Stragene hNT neuron (#937233) *Homo sapiens* cDNA clone IMAGE:648168 5', mRNA sequence.

GenBank™ Accession No. S45038 protein disulfide–isomerase homolog P5 precursor—rat (fragment).

GenBank™ Accession No. AAA29126 for alpha–phosophoinositide–specific phospholipase C–like.

GenBank™ Accession No. P38660 for probable protein disulfide isomerase P5 precursor.

GenBank™ Accession No. AAB05641 for protein disulphide isomerase PDI.

GenBank™ Accession No. CAA38402 for protein disulphide isomerase.

GenBank™ Accession No. P55059 for protein disulphide isomerase precursor.

GenBank™ Accession No. CAA10978 for protein disulphide isomerase.

GenBank™ Accession No. AAA35169 for TRG1.

GenBank™ Accession No. AAB50217 for protein disulfide isomerase–related protein 5.

GenBank™ Accession No. CAB07481 for predicted using Genefinder; similarity to mouse chromodomain–helicase–DNA–building protein.

GenBank™ Accession No. AAA34848 for protein disulphide isomerase.

GenBank™ Accession No. Q63081 for probable protein disulfide isomerase p5 precursor.

GenBank™ Accession No. AAC37215 for disulfide–like protein.

GenBank™ Accession No. P17967 for protein disulfide isomerase precursor.

GenBank™ Accession No. Q15084 for probable protein disulfide isomerase p5 precursor.

GenBank™ Accession No. Q10057 for Putative protein disulfide isomerase C1F5.02 precursor.

GenBank™ Accession No. AA263131 for PMY0593 KG1–a Lambda Zap Express cDNA library *Homo sapiens* cDNA 5', mRNA sequence.

GenBank™ Accession No. 3217991 for Y49E10.j.

GenBank™ Accession No. L28174 for *Acanthamoeba castallanii* disulfide–like protein mRNA.

GenBank™ Accession No. Z98044 for *Homo sapiens* chromosome 1 clone 510D11, working draft sequence.

GenBank™ Accession No. X64346 for Herpesvirus Saimiri complete genome DNA.

GenBank™ Accession No. J03998 for *P.falciparum* glutamic acid–rich protein gene.

GenBank™ Accession No. M86409 for herpesvirus Saimiri the most three prime end of the genome.

GenBank™ Accession No. U19361 for *Petromyzon marinus* neurofilament subunit nf–180 mRNA.

GenBank™ Accession No. S76368 for ORF 5' of ECLF2 . . . ECRF3=G protein–coupled receptor homolog.

GenBank™ Accession No. G37798 for *P.falciparum* haploid *P. falciparum* STS genomic, sequence tagged site.

Copy of BLAST® search (EST Database) using the MP–4 Nucleic Acid Sequence.

Copy of BLAST® search (EST Database) using the MP–4cds Nucleic Acid Sequence.

Copy of BLAST® search (NRN Database) using the MP–4nuc Nucleic Acid Sequence.

Copy of BLAST® search (NRN Database) using the MP–4 Nucleic Acid Sequence.

Copy of BLAST® search (NRP Database) using the MP–4 Amino Acid Sequence.

Copy of BLAST® search (NRN Database) using the MP–4pep Amino Acid Sequence.

Claudio, J.O. et al. "Identification of sequence–tagged transcripts differentially expressed within the human hematopoietic hierarchy," 1998, *Genomics*, 50(1):44–52.

Farquhar, R. et al., "Protein disulfide isomerase is essential for viability in *Saccharomyces cerevisiae*," 1991, *Gene*, 108(1):81–89.

Ferrari, S. et al., "The active gene that encodes human high mobility group 1 protein (HMG1) contains introns and maps to chromosome 13," 1996, *Genomics*, 35(2):367–371.

Fullekrug, J. et al., "CaBP1, a calcium binding protein of the thioredoxin family, is a resident KDEL protein of the ER and not of the intermediate compartment," 1994, *J. Cell Sci.*, 107:2719–2727.

Gardner, M.J. et al., "Chromosome 2 sequence of the human malaria parasite *Plasmodium falciparum*," 1998, *Science*, 282(5391):1126–1132.

Gunther, R. et al., "The *Saccharomyces cerevisiae* TRG1 gene is essential for growth and encodes a lumenal endoplasmic reticulum glycoprotein involved in the maturation of vacuolar carboxypeptidase," 1991, *J. Biol. Chem.*, 266:24557–24563.

Hayano, T. et al., "Cloning and sequencing of the cDNA encoding human P5," 1995, *Gene*, 164(2):377–378.

Jacobs, A.J. et al., "The single lamprey neurofilament subunit (NF–180) lacks multiphosphorylation repeats and is expressed selectively in projection neurons," 1995, *Brain res. Mol. Brain res.*, 29(1):43–52.

Kajino, T. et al., "Molecular cloning of a fungal cDNA encoding protein disulfide isomerase," 1994, *Biosci. Biotechnol. Biochem.*, 58(8):1424–1429.

Klobutcher, L.A. et al., "Sequence of a *Euplotes crassus* macronuclear DNA molecule encoding a protein with homology to a rat form–I phosphoinositide–specific phospholipase C," 1991, *J. Protozool*, 38(4):425–427.

Koch, A.W. et al., "Spinalin, a new glycine– and histidine–rich protein in spines of *Hydra nematocysts*," 1998, *J. Cell Sci.*, 111:1545–1554.

LaMantia, M. et al., "Glycosylation site binding protein and protein disulfide isomerase are identical and essential for cell viability in yeast," 1991, *PNAS*, 88:4453–4457.

Matsuoka, K. et al., "A nuclear factor containing the leucine–rich repeats expressed in murine cerebellar neurons," 1994, *PNAS*, 91(21):9670–9674.

Nicholas, J. et al., "Herpesvirus saimiri encodes homologues of G protein–coupled receptors and cyclins," 1992, *Nature*, 355(6358):362–365.

Nicholas, J. et al., "Analysis of nucleotide sequence of the rightmost 43 kbp of herpesvirus saimiri (HVS) L–DNA: general conservation of genetic organization between HVS and Epstein–Barr virus," 1992, *Virology*, 188:296–310.

Purnelle, B. et al., "The sequence of 55 kb on the left arm of yeast chromosome XVI identifies a small nuclear RNA, a new putative protein kinase and two new putative regulators," 1996, *Yeast*, 12(14):1483–1492.

Sasaki, N. et al., "Characterization of gene expression in mouse blastocyst using single–pass sequencing of 3995 clones," 1998, *Genomics*, 49(2):167–179.

Tachikawa, H. et al., "Molecular structure of a yeast gene, PDII, encoding protein disulfide isomerase that is essential for cell growth," 1991, *J. Biochem.*, 110(2):306–313.

Thomas, P.J. et al., "Defective folding as a basis of human disease," *TIBS*, 20:456–459 (1995).

Triglia, T. et al., "Structure of a *Plasmodium falciparum* gene that encodes a glutamic acid–rich protein (GARP)," 1988, *Mol. Biochem. Parasitol.*, 31:199–202.

Wen, L. et al., "A human placental cDNA clone that encodes nonhistone chromosomal protein HMG–1," 1989, *Nucleic Acids Res.*, 17(3):1197–1214.

Wilson, R. et al., "2.2 Mb of contiguous nucleotide sequence from chromosome III of *C. elegans*," 1994, *Nature*, 368(6466):32–38.

Xiang, Y.Y. et al., "Expression of high–mobility group–1 mRNA in human gastrointestinal adenocarcinoma and corresponding non–cancerous mucosa," 1997, *Int. J. Cancer*, 74(1):1–6.

Agostino et al.(Oct. 15, 1998, WO9845436) Accesion V89225 (Sequence search).

Adams al., (Apr. 21, 1997) Accession No. AA356542 (Sequence search).

Figure 1

SEQ ID NO:1

GCCCACGCGTCCGCCCGCGAGGGCGGAAGTGGGAGCTGCGACCGCGCTCCCTGTGAGGTGGGCAA
GCGGCGAAATGGCGCCCTCCGGGAGTCTTGCAGTTCCCCTGGCAGTCCTGGTGCTGTTGCTTTGG
GGTGCTCCCTGGACGCACGGGCGGCGGAGCAACGTTCGCGTCATCACGGACGAGAACTGGAGAGA
ACTGCTGGAAGGAGACTGGATGATAGAATTTTATGCCCCGTGGTGCCCTGCTTGTCAAAATCTTC
AACCGGAATGGGAAAGTTTTGCTGAATGGGGAGAAGATCTTGAGGTTAATATTGCGAAAGTAGAT
GTCACAGAGCAGCCAGGACTGAGTGGACGGTTTATCATACTGCTCTTCCTACTATTTATCTGTAA
AGATGGTGAATTTAGGCGCTATCAGGGTCCAAGGACTAAGAAGGACTTCATAAACTTTATAAGTG
ATAAAGAGTGGAAGAGTATTGAGCCCGTTTCATCATGGTTTGGTCCAGGTTCTGTTCTGATGAGT
AGTATGTCAGCACTCTTTCAGCTATCTATGTGGATCAGGACGTGCCATAACTACTTTATTGAAGA
CCTTGGATTGCCAGTGTGGGGATCATATACTGTTTTTGCTTTAGCAACTCTGTTTTCCGGACTGT
TATTAGGACTCTGTATGATATTTGTGGCAGATTGCCTTTGTCCTTCAAAAAGGCGCAGACCACAG
CCATACCCATACCCTTCAAAAAAATTATTATCAGAATCTGCACAACCTTTGAAAAAAGTGGAGGA
GGAACAAGAGGCGGATGAAGAAGATGTTTCAGAAGAAGAAGCTGAAAGTAAAGAAGGAACAAACA
AAGACTTTCCACAGAATGCCATAAGACAACGCTCTCTGGGTCCATCATTGGCCCAGATAAATCCT
AGTTAAATTTTATAGTTATCTTAATATTATGATTTTGATAAAAACAGAAGATTGATCATTTTGTT
TGGTTTGAAGTGAACTGGACTTTTTTGAATATTGCAGGGTTCAGTCTAGATTGTCATTAAATTGA
AGAGTCTACNTTCAGAACATAAAAGCACTAGGTATACAAGTTTGAAATATGATTTAAGCACAGTA
TGATGGTTTAAATAGTTCTCTAATTTTTGAAAAATCGTGCCAAGCAATAAGATTTATGTATATTT
GTTTAATAATAACCTATTTCAAGTCTGAGTTTTGAAA

SEQ ID NO:2

MAPSGSLAVPLAVLVLLLWGAPWTHGRRSNVRVITDENWRELLEGDWMIEFYAPWCPACQNLQPE
WESFAEWGEDLEVNIAKVDVTEQPGLSGRFIILLFLLFICKDGEFRRYQGPRTKKDFINFISDKE
WKSIEPVSSWFGPGSVLMSSMSALFQLSMWIRTCHNYFIEDLGLPVWGSYTVFALATLFSGLLLG
LCMIFVADCLCPSKRRRPQPYPYPSKKLLSESAQPLKKVEEEQEADEEDVSEEEAESKEGTNKDF
PQNAIRQRSLGPSLAQINPS.

SEQ ID NO:3

ATGGCGCCCTCCGGGAGTCTTGCAGTTCCCCTGGCAGTCCTGGTGCTGTTGCTTTGGGGTGCTCC
CTGGACGCACGGGCGGCGGAGCAACGTTCGCGTCATCACGGACGAGAACTGGAGAGAACTGCTGG
AAGGAGACTGGATGATAGAATTTTATGCCCCGTGGTGCCCTGCTTGTCAAAATCTTCAACCGGAA
TGGGAAAGTTTTGCTGAATGGGGAGAAGATCTTGAGGTTAATATTGCGAAAGTAGATGTCACAGA
GCAGCCAGGACTGAGTGGACGGTTTATCATACTGCTCTTCCTACTATTTATCTGTAAAGATGGTG
AATTTAGGCGCTATCAGGGTCCAAGGACTAAGAAGGACTTCATAAACTTTATAAGTGATAAAGAG
TGGAAGAGTATTGAGCCCGTTTCATCATGGTTTGGTCCAGGTTCTGTTCTGATGAGTAGTATGTC
AGCACTCTTTCAGCTATCTATGTGGATCAGGACGTGCCATAACTACTTTATTGAAGACCTTGGAT
TGCCAGTGTGGGGATCATATACTGTTTTTGCTTTAGCAACTCTGTTTTCCGGACTGTTATTAGGA
CTCTGTATGATATTTGTGGCAGATTGCCTTTGTCCTTCAAAAAGGCGCAGACCACAGCCATACCC
ATACCCTTCAAAAAAATTATTATCAGAATCTGCACAACCTTTGAAAAAAGTGGAGGAGGAACAAG
AGGCGGATGAAGAAGATGTTTCAGAAGAAGAAGCTGAAAGTAAAGAAGGAACAAACAAAGACTTT
CCACAGAATGCCATAAGACAACGCTCTCTGGGTCCATCATTGGCCCAGATAAATCCTAGTTAA

Figure 2

```
     ssvvvvltdenFdeevlkaksdkpVLVdFyApWCGpCKmlAPeyekl
       s v v+tden+ e l      +++++++FyApWC  C++l Pe+e +
  28 RSNVRVITDENWRE--LL---EGDWMIEFYAPWCPACQNLQPEWESF 69

Aqeykgesd.dvkfaKVDaDenpkdlAskygVrgfPTlkff.knGkkepv
      A+       d v +aKVD++e+p  l   ++ +  f   l+f+ k+G+
  70 AEWGE---DlEVNIAKVDVTEQP-GLSGRFIILLF--LLFIcKDGEF--R 111 dyvgGArtkddLvafi
      y+g+ rtk d+++fi
 112 RYQGP-RTKKDFINFI 126
```

THIOREDOXIN FAMILY ACTIVE SITE MOLECULES AND USES THEREFOR

BACKGROUND OF THE INVENTION

Thioredoxin family active site proteins are a superfamily of proteins that participate in redox reactions and are distributed among a wide range of living organisms (Holmgren, A. (1985) *Ann. Rev. Biochem.* 54:237–271; Eklund, H. et al. (1991) *Proteins* 11:13–28; Freedman, R. B. et al. (1994) *Trends in Biochem. Sci.* 19:331–336). The thioredoxin family active site is characterized by a CXXC motif (C represents cysteine and X represents any of the 20 amino acids incorporated into proteins). The neighboring cysteine residues cycle between a reduced sulfhydryl and an oxidized disulfide form.

The reduced form of thioredoxin is known to activate some enzymes by reducing disulfide bridges that control their activity. In addition, thioredoxin is an electron donor in the reaction sequence that reduces ribonucleotides to deoxyribonucleotides catalyzed by ribonucleotide reductase (Stryer, L. (1995) *Biochemistry* 4th Edition, W.H. Freeman and Company, pages 677, and 750–751.). It has been reported that in humans, thioredoxin and the cellular redox state modified by thioredoxin play a crucial role in arterial neointima formation in atherosclerosis (Takagi, Y. et al. (1998) *Laboratory Investigation* 78:957–66). Thioredoxin is believed to be involved in cellular defense mechanisms against oxidative damage (see, for example, Tanaka, T. et al. (1997) *Laboratory Investigation* 77:145–55). Thioredoxin has also been implicated in regulating glucocorticoid responsiveness to cellular oxidative stress response pathways. In particular, thioredoxin is believed to be capable of sensing, and transmitting, the redox state of the cell, to the glucocorticoid receptor by targeting both the ligand- and DNA-binding domains of the receptor (Makino, Y. et al. (1996) *Journal of Clinical Investigation* 98:2469–77). Human thioredoxin has been suggested to act as a free radical scavenger and has been shown to limit the extent of ischaemia reperfusion injury (Fukuse, T. et al. (1995) *Thorax* 50:387–91).

Protein disulfide isomerases are an important class of thioredoxin family active site-containing proteins that catalyze the oxidation of thiols, reduction of disulfide bonds, and isomerization of disulfides, depending on the reaction conditions (Freedman, R. B. et al. (1994) *Trends in Biochem. Sci.* 19:331–336).

Protein disulfide isomerases catalyze the formation of correct disulfide pairings in nascent proteins. Protein disulfide isomerases preferentially interact with peptides that contain cysteine residues but are otherwise undiscriminating. The broad substrate specificity of protein disulfide isomerases enables them to speed the folding of diverse disulfide-containing proteins. By shuffling disulfide bonds, protein disulfide isomerases enable proteins to quickly find the most thermodynamically stable pairings amongst those that are accessible. Consequently, protein disulfide isomerases are involved in protein processing, protein folding, and protein secretion. Certain protein disulfide isomerases are also involved in collagen and collagen-like protein biosynthesis because a protein disulfide isomerase is a subunit of prolyl 4-hydroxylase, a collagen and collagen-like protein biosynthetic enzyme (Kivirikko, K. I. et al. (1998) *Matrix Biol.* 16:357–368; Kivirikko, K. I. et al. (1998) *Adv. Enzymol. Relat. Areas Mol. Biol.* 72:325–398). Because mutations in prolyl 4-hydroxylase cause Ehlers-Danlos Syndrome, protein disulfide isomerases have been implicated in Ehlers-Danlos Syndrome.

Given the important biological roles and properties of thioredoxin family active site-containing proteins, there exists a need for the identification of novel genes encoding such proteins as well as for the discovery of modulators of such molecules for use in regulating a variety of normal and/or pathological cellular processes.

SUMMARY OF THE INVENTION

The present invention is based, at least in part, on the discovery of novel members of the thioredoxin family active site molecules, referred to herein as MP-4 nucleic acid and protein molecules. The MP-4 nucleic acid and protein molecules of the present invention are useful as targets for developing modulating agents that regulate a variety of cellular processes, e.g., cellular redox reactions. Accordingly, in one aspect, this invention provides isolated nucleic acid molecules encoding MP-4 polypeptides or biologically active portions thereof, as well as nucleic acid fragments suitable as primers or hybridization probes for the detection of MP-4-encoding nucleic acids.

In one embodiment, a MP-4 nucleic acid molecule of the invention is at least 60%, 65%, 70%, 75%, 80%, 85%, 90%, 91%, 92%, 93%, 94%, 95%, 96%, 97%, 98%, 99% or more homologous to the nucleotide sequence (e.g., to the entire length of the nucleotide sequence) shown in SEQ ID NO:1, SEQ ID NO:3, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1–73 of SEQ ID NO:1. In yet another embodiment, the nucleic acid molecule includes SEQ ID NO:3 and nucleotides 917–1207 of SEQ ID NO:1. In another preferred embodiment, the nucleic acid molecule has the nucleotide sequence shown in SEQ ID NO:1 or 3. In another preferred embodiment, the nucleic acid molecule includes a fragment of at least 395 nucleotides of the nucleotide sequence of SEQ ID NO:1, SEQ ID NO:3, or a complement thereof.

In another embodiment, a MP-4 nucleic acid molecule includes a nucleotide sequence encoding a protein having an amino acid sequence sufficiently homologous to the amino acid sequence of SEQ ID NO:2. In a preferred embodiment, a MP-4 nucleic acid molecule includes a nucleotide sequence encoding a protein having an amino acid sequence at least 60%, 65%, 70%, 75%, 80%, 85%, 90%, 95% or more homologous to the amino acid sequence of SEQ ID NO:2.

In another preferred embodiment, an isolated nucleic acid molecule encodes the amino acid sequence of human MP-4. In yet another preferred embodiment, the nucleic acid molecule includes a nucleotide sequence encoding a protein having the amino acid sequence of SEQ ID NO:2. In yet another preferred embodiment, the nucleic acid molecule is at least 842 nucleotides in length and encodes a protein having a MP-4 activity (as described herein).

Another embodiment of the invention features nucleic acid molecules, preferably MP-4 nucleic acid molecules, which specifically detect MP-4 nucleic acid molecules relative to nucleic acid molecules encoding non-MP-4 proteins. For example, in one embodiment, such a nucleic acid molecule is at least 395, 400–450, 450–500, 500–550, 550–600, 600–650, 650–700, 700–750, 750–800 or more nucleotides in length and hybridizes under stringent conditions to a nucleic acid molecule comprising the nucleotide sequence shown in SEQ ID NO:1, or a complement thereof, or a complement thereof In preferred embodiments, the nucleic acid molecules are at least 15 (e.g., contiguous) nucleotides in length and hybridize under stringent conditions to nucleotides 1–78 and 973–976 of SEQ ID NO:1. In other preferred embodiments, the nucleic acid molecules comprise nucleotides 1–78 and 973–976 of SEQ ID NO:1.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or SEQ ID NO:3 under stringent conditions.

Another embodiment of the invention provides an isolated nucleic acid molecule which is antisense to a MP-4 nucleic acid molecule, e.g., the coding strand of a MP-4 nucleic acid molecule.

Another aspect of the invention provides a vector comprising a MP-4 nucleic acid molecule. In certain embodiments, the vector is a recombinant expression vector. In another embodiment, the invention provides a host cell containing a vector of the invention. The invention also provides a method for producing a protein, preferably a MP-4 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant MP-4 proteins and polypeptides. In one embodiment, the isolated protein, preferably a MP-4 protein, includes at least one thioredoxin family active site. In another embodiment, the isolated protein, preferably a MP-4 protein, includes at least one transmembrane domain. In another embodiment, the isolated protein, preferably a MP-4 protein, includes at least one thioredoxin family active site and at least one transmembrane domain. In another embodiment, the isolated protein, preferably a MP-4 protein, includes at least one thioredoxin family active site; at least one transmembrane domain; at least one protein phosphorylation site selected from the group consisting of a Protein Kinase C site, a Casein Kinase II site, and a tyrosine kinase phosphorylation site; at least one N-myristoylation site; and at least one amidation site. In a preferred embodiment, the protein, preferably a MP-4 protein, includes at least one thioredoxin family active site and at least one transmembrane domain and has an amino acid sequence at least about 60%, 65%, 70%, 75%, 80%, 85%, 90%, 95% or more homologous to the amino acid sequence of SEQ ID NO:2.

In another preferred embodiment, the protein, preferably a MP-4 protein, includes at least one thioredoxin family active site and plays a role in regulating cellular redox reactions, e.g., catalyzing the oxidation of a thiol group and/or the reduction of a disulfide bond of a target protein, modulating enzymatic activity, or modulating protein processing, folding and/or secretion. In another preferred embodiment, the protein, preferably a MP-4 protein, includes at least one transmembrane domain and plays a role in regulating cellular redox reactions, e.g., catalyzing the oxidation of a thiol group and/or the reduction of a disulfide bond of a target protein, modulating enzymatic activity, or modulating protein processing, folding and/or secretion. In another preferred embodiment, the protein, preferably a MP-4 protein, includes at least one thioredoxin family active site and at least one transmembrane domain, and plays a role in cellular redox reactions, e.g., catalyzing the oxidation of a thiol group and/or the reduction of a disulfide bond of a target protein, modulating enzymatic activity, or modulating protein processing, folding and/or secretion. In yet another preferred embodiment, the protein, preferably a MP-4 protein, includes at least one thioredoxin family active site and at least one transmembrane domain and is encoded by a nucleic acid molecule having a nucleotide sequence which hybridizes under stringent hybridization conditions to a nucleic acid molecule comprising the nucleotide sequence of SEQ ID NO:1, or SEQ ID NO:3.

In another embodiment, the invention features fragments of the proteins having the amino acid sequence of SEQ ID NO:2, wherein the fragment comprises at least 15 amino acids (e.g., contiguous amino acids) of the amino acid sequence of SEQ ID NO:2. In another embodiment, the protein, preferably a MP-4 protein, has the amino acid sequence of SEQ ID NO:2.

In another embodiment, the invention features an isolated protein, preferably a MP-4 protein, which is encoded by a nucleic acid molecule having a nucleotide sequence at least about 60%, 65%, 70%, 75%, 80%, 85%, 90%, 95% or more homologous to a nucleotide sequence of SEQ ID NO:1, SEQ ID NO:3, or a complement thereof. This invention further features an isolated protein, preferably a MP-4 protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, or a complement thereof.

The proteins of the present invention or biologically active portions thereof, can be operatively linked to a non-MP-4 polypeptide (e.g., heterologous amino acid sequences) to form fusion proteins. The invention further features antibodies, such as monoclonal or polyclonal antibodies, that specifically bind proteins of the invention, preferably MP-4 proteins. In addition, the MP-4 proteins or biologically active portions thereof can be incorporated into pharmaceutical compositions, which optionally include pharmaceutically acceptable carriers.

In another aspect, the present invention provides a method for detecting the presence of a MP-4 nucleic acid molecule, protein or polypeptide in a biological sample by contacting the biological sample with an agent capable of detecting a MP-4 nucleic acid molecule, protein or polypeptide such that the presence of a MP-4 nucleic acid molecule, protein or polypeptide is detected in the biological sample.

In another aspect, the present invention provides a method for detecting the presence of MP-4 activity in a biological sample by contacting the biological sample with an agent capable of detecting an indicator of MP-4 activity such that the presence of MP-4 activity is detected in the biological sample.

In another aspect, the invention provides a method for modulating MP-4 activity comprising contacting a cell capable of expressing MP-4 with an agent that modulates MP-4 activity such that MP-4 activity in the cell is modulated. In one embodiment, the agent inhibits MP-4 activity. In another embodiment, the agent stimulates MP-4 activity. In one embodiment, the agent is an antibody that specifically binds to a MP-4 protein. In another embodiment, the agent modulates expression of MP-4 by modulating transcription of a MP-4 gene or translation of a MP-4 mRNA. In yet another embodiment, the agent is a nucleic acid molecule having a nucleotide sequence that is antisense to the coding strand of a MP-4 mRNA or a MP-4 gene.

In one embodiment, the methods of the present invention are used to treat a subject having a disorder characterized by aberrant MP-4 protein or nucleic acid expression or activity by administering an agent which is a MP-4 modulator to the subject. In one embodiment, the MP-4 modulator is a MP-4 protein. In another embodiment the MP-4 modulator is a MP-4 nucleic acid molecule. In yet another embodiment, the MP-4 modulator is a peptide, peptidomimetic, or other small molecule. In a preferred embodiment, the disorder characterized by aberrant MP-4 protein or nucleic acid expression is a cardiovascular disorder, e.g., atherosclerosis, ischaemia reperfusion injury, cardiac hypertrophy, hypertension, coronary artery disease, myocardial infarction, arrythmia, cardiomyopathies, and congestive heart failure; a connective tissue disorder, e.g., Ehlers-Danlos Syndrome; or a hepatic disorder, e.g., alcoholic liver disease, liver cirrhosis and liver cancer.

The present invention also provides a diagnostic assay for identifying the presence or absence of a genetic alteration characterized by at least one of (i) aberrant modification or mutation of a gene encoding a MP-4 protein; (ii) misregulation of the gene; and (iii) aberrant post-translational modification of a MP-4 protein, wherein a wild-type form of the gene encodes a protein with a MP-4 activity.

In another aspect the invention provides a method for identifying a compound that binds to or modulates the activity of a MP-4 protein, by providing an indicator composition comprising a MP-4 protein having MP-4 activity, contacting the indicator composition with a test compound, and determining the effect of the test compound on MP-4 activity in the indicator composition to identify a compound that modulates the activity of a MP-4 protein.

Other features and advantages of the invention will be apparent from the following detailed description and claims.

BRIEF DESCRIPTION OF THE DRAWINGS

FIG. 1 depicts the cDNA sequence (SEQ ID NO:1) and predicted amino acid sequence (SEQ ID NO:2) of the human MP-4. The methionine-initiated open reading frame of human MP-4 (without the 5' and 3' untranslated regions) extends from nucleotide 74 to nucleotide 916 of SEQ ID NO:1 (shown herein as SEQ ID NO:3).

FIG. 2 depicts an alignment of a portion of the amino acid sequence of the human MP-4 and a thioredoxin active site domain consensus sequence derived from a hidden Markov model (PF00085) (SEQ ID NO:6). The upper sequence in the alignment is the PF00085 sequence while the lower sequence corresponds to amino acid 28 to 126 of SEQ ID NO:2.

DETAILED DESCRIPTION OF THE INVENTION

Figure 3:
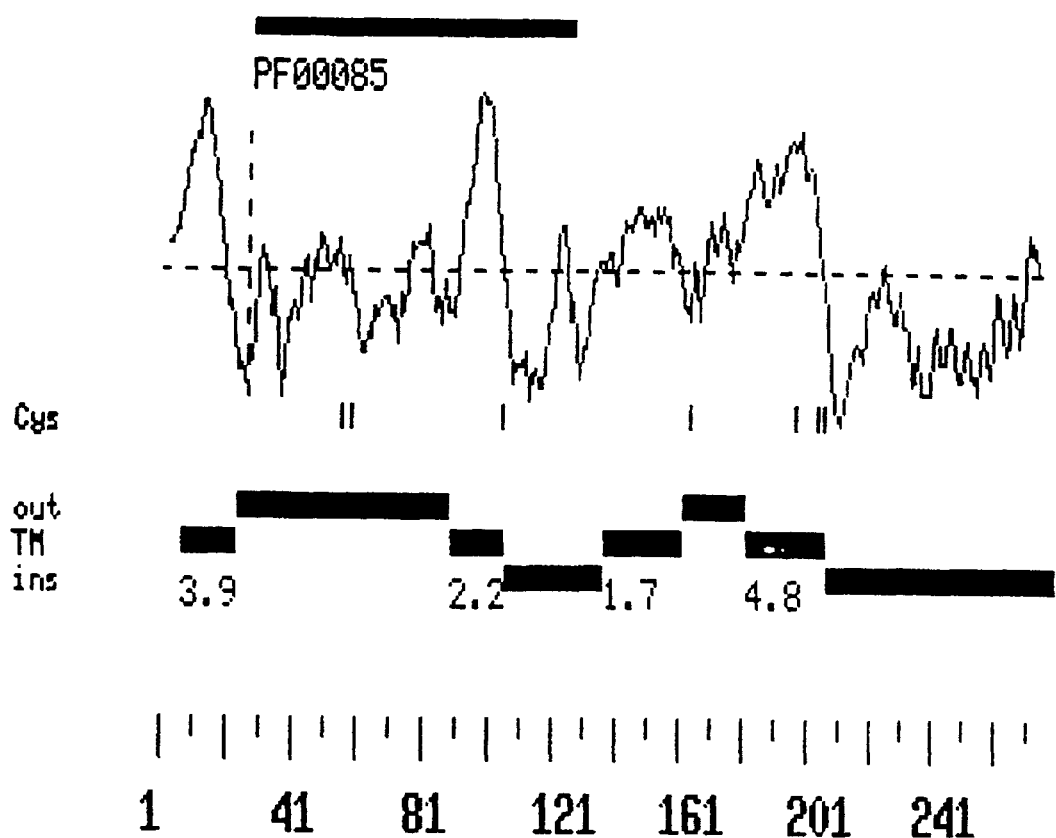
FIG. 3 shows a hydrophobicity analysis of the human MP-4 amino acid sequence (SEQ ID NO:2). Relative hydrophobicity is shown above the dotted line, and relative hydrophilicity is shown below the dotted line. An alignment with PF00085 indicates the presence of a thioredoxin active active site domain. The location of cysteine residues is indicated in the plot, as well as the approximate locations of extracellular (out), transmembrane (TM) and intracellular (Ins) regions. The corresponding amino acid numbering is indicated at the bottom of the figure.

The present invention is based, at least in part, on the discovery of novel molecules, referred to herein as MP-4 nucleic acid and protein molecules, which are novel members of the thioredoxin active site superfamily. These novel molecules are capable of, for example, regulating cellular redox reactions of a target, e.g., a protein, e.g., an enzyme, and thereby modulating cellular processes, such as enzymatic activity, protein processing, folding and/or secretion.

As used herein, a "thioredoxin active site superfamily" includes a group of proteins that include an active site characteristic of the thioredoxin family. The thioredoxin family active site is characterized by a CXXC motif, wherein C represents a cysteine residue and X represents any amino acid (Holmgren, A. (1985) *Ann. Rev. Biochem.* 54:237–271; Eklund, H. et al. (1991) *Proteins* 11:13–28; Freedman, R. B. et al. (1994) *Trends in Biochem. Sci.* 19:331–336). The cysteine residues neighboring this motif cycle between a reduced sulfhydryl and an oxidized disulfide form. Thioredoxin family members are typically involved in regulating, sensing and/or transmitting the redox state in a cell. For example, thioredoxin active site family members can (i) catalyze the oxidation of a thiol group and/or the reduction of a disulfide bond of a target protein or polypeptide, e.g., an enzyme; (ii) modulate enzymatic activity; (iii) prevent and/or ameliorate cellular oxidative damage; (iii) act as scavenger of free radicals; and/or (iv) regulate protein processing, folding and/or secretion. Examples of thioredoxin active site proteins include protein disulfide isomerases. Protein disulfide isomerases have been shown to catalyze the oxidation of thiols, reduction of disulfide bonds, and isomerization of disulfides, depending on the reaction conditions (Freedman, R. B. et al. (1994) *Trends in Biochem. Sci.* 19:331–336). For example, protein disulfide isomerases can catalyze the formation of correct disulfide pairings in nascent proteins. By shuffling disulfide bonds, protein disulfide isomerases enable proteins to quickly find the most thermodynamically stable pairings amongst those that are accessible.

As the MP-4 proteins of the present invention may modulate thioredoxin active site-mediated activities, they may be useful for developing novel diagnostic and therapeutic agents for thioredoxin active site associated disorders.

As used herein, a "thioredoxin active site associated disorder" includes a disorder, disease or condition which is characterized by a misregulation of a thioredoxin active site-mediated activity. Thioredoxin active site associated disorders can detrimentally affect the regulation, sensing and/or transmission of the redox state in a cell. Examples of thioredoxin active site associated disorders include cardiovascular disorders, e.g., atherosclerosis, ischaemia reperfusion injury, cardiac hypertrophy, hypertension, coronary artery disease, myocardial infarction, arrythmia, cardiomyopathies, and congestive heart failure; connective tissue disorders, e.g., Ehlers-Danlos Syndrome; and hepatic disorders, e.g., alcoholic liver disease, liver cirrhosis, liver cancer.

As used herein, a "thioredoxin active site mediated activity" includes an activity which involves a thioredoxin active site family member, associated with the regulation, sensing and/or transmission of the redox state of a cell in, for example, the cardiovascular system. Thioredoxin active site mediated activities include the modulation of enzymatic activity; modulation of the oxidation of thiol groups and/or reduction of disulfide bonds; modulation of protein disulfide isomerization; regulation of protein processing, protein folding, and/or protein secretion; prevention and/or amelioration of cellular oxidative damage; modulation of free radical concentrations; and modulation of cardiovascular activities.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of MP-4 proteins includes at least one "thioredoxin family active site". As used herein, the term "thioredoxin family active site" includes an amino acid sequence of at least about 90 amino acid residues in length which includes a CXXC motif, wherein C represents cysteine and X represents any of the 20 amino acids. More preferably, a thioredoxin family active site includes about at least 95, 98, 100, 105, 110, 115 or 120 amino acid residues and includes a CXXC motif. CXXC motifs are described in Holmgren, A. (1985) *Ann. Rev. Biochem.* 54:237–271; Eklund, H. et al. (1991) *Proteins* 11:13–28; Freedman, R. B. et al. (1994) *Trends in Biochem. Sci.* 19:331–336), the contents of which are incorporated herein by reference. About amino acid residues 28–126 of the human MP-4 protein (SEQ ID NO:2) comprise a thioredoxin family active site.

In another embodiment, the MP-4 protein includes at least one "transmembrane domain", preferably two transmembrane domains, and most preferably three transmembrane domains. As used herein, the term "transmembrane domain" includes an l amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, htto://pfam.wustl.edu/cgi-bin/getdesc?name=7tm-1, the contents of which are incorporated herein by reference. About amino acid residues 89–105, 137–161, and 182 206 of the human MP-4 protein (SEQ ID NO:2) comprise transmembrane domains.

In a preferred embodiment, the MP-4 molecules of the invention include a thioredoxin family active site and one, two, and preferably, three transmembrane domains. The MP-4 molecules of the present invention can fijrther include at least one protein phosphorylation site, for example, at least one, two, three, four, five and preferably, six Protein Kinase C sites, at least one, two, three, four, and preferably, five Casein Kinase II sites, and at least one tyrosine kinase phosphorylation site; at least one N-myristoylation site, and at least one and preferably two N-myristoylation sites; at least one amidation site; and optionally, a signal sequence. For example, MP-4 contains predicted Protein Kinase C sites at about amino acids 92–94, 118–120, 127–129, 208–210, 220–222 and 256–258 of SEQ ID NO:2; predicted Casein Kinase II sites are located at about amino acids 68–71, 118–121, 127–130, 246–249 and 256–259 of SEQ ID NO:2; one tyrosine kinase phosphopyration site from about amino acids 106–114 of SEQ ID NO:2; two N-myristoylation sites from about amino acids 20–25 and 191–196 of SEQ ID NO:2; and one amidation site from about amino acids 25–28 of SEQ ID NO:2.

In yet another embodiment, the MP-4 molecule can further include a signal sequence. As used herein, a "signal sequence" refers to a peptide of about 20–30 amino acid residues in length which occurs at the N-terminus of secretory and integral membrane proteins and which contains a majority of hydrophobic amino acid residues. For example, a signal sequence contains at least about 15–45 amino acid residues, preferably about 20–40 amino acid residues, more preferably about 25–35 amino acid residues, and more preferably about 28–32 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, an MP-4 protein contains a signal sequence of about amino acids 7–23 of SEQ ID NO:2. The "signal sequence" is cleaved during processing of the mature protein. The mature MP-4 protein corresponds to amino acids 24 to 280 of SEQ ID NO:2.

Isolated proteins of the present invention, preferably MP-4 proteins, have an amino acid sequence sufficiently homologous to the amino acid sequence of SEQ ID NO:2, or are encoded by a nucleotide sequence sufficiently homologous to SEQ ID NO:1, or SEQ ID NO:3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 60% homology, preferably 65% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 60%, preferably 65%, more preferably 70–80%, or 90–95% homology and share a common functional activity are defined herein as sufficiently homologous.

As used interchangeably herein, a "MP-4 activity", "biological activity of MP-4" or "functional activity of MP-4", refers to an activity exerted by a MP-4 protein, polypeptide or nucleic acid molecule on a MP-4 responsive cell or on a MP-4 protein substrate, as determined in vivo, or in vitro, according to standard techniques. In one embodiment, a MP-4 activity is a direct activity, such as an association with a MP-4-target molecule. As used herein, a "target molecule" or "binding partner" is a molecule with which a MP-4 protein binds or interacts in nature, such that MP-4-mediated function is achieved. A MP-4 target molecule can be a non-MP-4 molecule or a MP-4 protein or polypeptide of the present invention. In an exemplary embodiment, a MP-4 target molecule is an enzyme. Alternatively, a MP-4 activity is an indirect activity, such as a cellular signaling activity mediated by interaction of the MP-4 protein with a MP-,4 enzyme. The biological activities of MP-4 are described herein. For example, the MP.-4 proteins of the present invention can have one or more of the following activities: (1) modulate enzymatic activity, (2) modulate protein processing and/or folding, (3) modulate protein secretion, (4) modulate protein disulfide isomerization, (5) catalyze the oxidation of a thiol group and/or the reduction of a disulfide bond of a target protein or polypeptide, (6) sense and/or transmit the redox state in a cell, (7) prevent and/or ameliorate cellular oxidative damage, (8) regulate free radical concentrations, and (9) modulate cardiovascular activities.

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

Accordingly, another embodiment of the invention features isolated MP-4 proteins and polypeptides having a MP-4 activity. Preferred proteins are MP-4 proteins having at least one thioredoxin family active site, at least one transmembrane domain, preferably, an MP-4 activity. Other preferred proteins are MP-4 proteins having at least one transmembrane domain and, preferably, a MP-4 activity. Other preferred proteins are MP-4 proteins having at least one thioredoxin family active site, and, preferably, a MP-4 activity. Other preferred proteins are MP-4 proteins having at least one transmembrane domain, at least one thioredoxin family active site, and are, preferably, encoded by a nucleic acid molecule having a nucleotide sequence which hybridizes under stringent hybridization conditions to a nucleic acid molecule comprising the nucleotide sequence of SEQ ID NO:1, or SEQ ID NO:3.

The nucleotide sequence of the isolated human MP-4 cDNA and the predicted amino acid sequence of the human MP-4 polypeptide are shown in FIG. 1 and in SEQ ID NOs:1 and 2, respectively.

The human MP-4 cDNA sequence (SEQ ID NO:1), which is approximately 1207 nucleotides long including untranslated regions, contains a predicted methionine-initiated coding sequence of about 843 nucleotides (nucleotides 74–916 of SEQ ID NO:1; SEQ ID NO:3) which encodes a 280 amino acid protein (SEQ ID NO:2) having a molecular weight of approximately 31,862 kDa (excluding post-translational modifications). The MP-4 protein of SEQ ID NO:2 includes an amino-terminal hydrophobic amino acid sequence, consistent with a signal sequence, of about 26 amino acids (from amino acid 1 to about amino acid 26 of SEQ ID NO:2), which upon protease removal results in the production of the mature protein.

The mature protein is approximately 254 amino acid residues in length (from about amino acid 27 to amino acid 280 of SEQ ID NO:2). The mature protein corresponding to MP-4 protein is predicted to have about 254 amino acids (from about amino acid 27 to amino acid 280 of SEQ ID NO:2; SEQ ID NO:5). MP-4 contains three transmembrane domains which extend from about amino acid 89 (extracellular end) to about amino acid 105 (cytoplasmic end) of SEQ ID NO:2; from about amino acid 137 (cytoplasmic end) to about amino acid 161 (extracellular end) of SEQ ID NO:2, and from about amino acid 182 (extracellular end) to about amino acid 206 (cytoplasmic end) of SEQ ID NO:2. MP-4 protein contains six predicted protein kinase C phosphorylation sites (PS00005) from amino acids 92–94, 118–120, 127–129, 208–210, 220–222, and 256–258 of SEQ ID NO:2; five casein kinase II phosphorylation sites (PS00006) from amino acids 68–71, 118–121, 127–130, 246–249, and 256–259 of SEQ ID NO:2; one tyrosine kinase phosphorylation site (PS00007) from amino acid 106–114, of SEQ ID NO:2; two N-myristoylation sites (PS00008) from amino acids 20–25 and 191–196 of SEQ ID NO:2; one amidation site (PS00009) from amino acid 25–28, of SEQ ID NO:2; and one thioredoxin active active site domain (PF00085) from about amino acid 28–126, of SEQ ID NO:2. For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

The human MP-4 gene is expressed in the human heart, skin, B- and T-cells, spleen, kidney, lung, bone, thymus and testis. The MP-4 nucleic acids and polypeptides of the invention may play roles in normal and pathological processes involving the cells and tissues that express them, or cells and tissues that contact said MP-4 polypeptides. For example, since MP-4 molecules are expressed in the heart, as shown in Example 2, MP-4 molecules may be involved in cardiovascular disorders including, but not limited to, atherosclerosis, ischaemia reperfusion injury, cardiac hypertrophy, hypertension, coronary artery disease, myocardial infarction, arrythmia, cardiomyopathies, and congestive heart failure.

Various aspects of the invention are described in fuirther detail in the following subsections:

I. Isolated Nucleic Acid Molecules

One aspect of the invention pertains to isolated nucleic acid molecules that encode MP-4 proteins or biologically active portions thereof, as well as nucleic acid fragments sufficient for use as hybridization probes to identify MP-4-encoding nucleic acid molecules (e.g., MP-4 mRNA) and fragments for use as PCR primers for the amplification or mutation of MP-4 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MP-4 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or SEQ ID NO:3, or a portion thereof, can be isolated using standard molecular biology techniques and the sequence information provided herein. Using all or portion of the nucleic acid sequence of SEQ ID NO:1, or SEQ ID NO:3, or SEQ ID NO:3, as a hybridization probe, MP-4 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3, or SEQ ID NO:3 can be isolated by the polymerase chain reaction (PCR) using synthetic oligonucleotide primers designed based upon the sequence of SEQ ID NO:1, or SEQ ID NO:3

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to MP-4 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human MP-4 cDNA. This cDNA comprises sequences encoding the human MP-4 protein (i.e., "the coding region", from nucleotides 74–1206), as well as 5' untranslated sequences (nucleotides 1–73) and 3' untranslated sequences (nucleotides 917–1207). Alternatively, the nucleic acid molecule can comprise only the coding region of SEQ ID NO:1 (e.g., nucleotides 74–1206, corresponding to SEQ ID NO:3).

In another preferred embodiment, an isolated nucleic acid molecule of the invention comprises a nucleic acid molecule which is a complement of the nucleotide sequence shown in SEQ ID NO:1, SEQ ID NO:3, or a portion of any of these nucleotide sequences. A nucleic acid molecule which is complementary to the nucleotide sequence shown in SEQ ID NO:1, or SEQ ID NO:3, is one which is sufficiently complementary to the nucleotide sequence shown in SEQ ID NO:1, SEQ ID NO:3, or SEQ ID NO:3, such that it can hybridize to the nucleotide sequence shown in SEQ ID NO:1, or SEQ ID NO:3, thereby forming a stable duplex.

In still another preferred embodiment, an isolated nucleic acid molecule of the present invention comprises a nucleotide sequence which is at least about 60%, 65%, 70%, 75%, 80%, 85%, 90%, 95% or more homologous to the entire length of the nucleotide sequence shown in SEQ ID NO:1, SEQ ID NO:3, or a portion of any of these nucleotide sequences.

A. MP-4 Nucleic Acid Fragments

Moreover, the nucleic acid molecule of the invention can comprise only a portion of the nucleic acid sequence of SEQ ID NO:1, or SEQ ID NO:3, for example a fragment which can be used as a probe or primer or a fragment encoding a biologically active portion of a MP-4 protein, e.g., a fragment comprising nucleotides 155 to 451 of SEQ ID NO:1, which encodes the thioredoxin active site domain of MP-4. The nucleotide sequence determined from the cloning of the MP-4 gene allows for the generation of probes and primers designed for use in identifying and/or cloning other MP-4 family members, as well as MP-4 homologues from other species.

The probe/primer typically comprises substantially purified oligonucleotide. The oligonucleotide typically comprises a region of nucleotide sequence that hybridizes under stringent conditions to at least about 12 to 15, preferably about 20 to 25, more preferably about 30, 35, 40, 45, 50, 55, 60, 65, or 75 consecutive nucleotides of a sense sequence of SEQ ID NO:1, or SEQ ID NO:3, of an anti-sense sequence of SEQ ID NO:1, or SEQ ID NO:3, or of a naturally occurring allelic variant or mutant of SEQ ID NO:1, or SEQ ID NO:3.

In an exemplary embodiment, a nucleic acid molecule of the present invention comprises a nucleotide sequence which is 395, 400, 400–450, 450–500, 500–550, 537, 550–600, 600–650, 650–700, 700–750, 750–800, 800–850, 850–900, 950–1000, 1100–1200 nucleotides in length and hybridizes under stringent hybridization conditions to a nucleic acid molecule of SEQ ID NO:1, or 395, 400, 400–450, 450–500, 500–550, 537, 550–600, 600–650, 650–700, 700–750, 750–800, 800–840 nucleotides in length and hybridizes under stringent hybridization conditions to a nucleic acid molecule of SEQ ID NO:3.

Probes based on the MP-4 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a MP-4 protein, such as by measuring a level of a MP-4-encoding nucleic acid in a sample of cells from a subject e.g., detecting MP-4 mRNA levels or determining whether a genomic MP-4 gene has been mutated or deleted.

A nucleic acid fragment encoding a "biologically active portion of a MP-4 protein" can be prepared by isolating a portion of the nucleotide sequence of SEQ ID NO:1, SEQ ID NO:3, or SEQ ID NO:3, which encodes a polypeptide having a MP-4 biological activity (the biological activities of the MP-4 proteins are described herein), expressing the encoded portion of the MP-4 protein (e.g., by recombinant expression in vitro) and assessing the activity of the encoded portion of the MP-4 protein. For example, a nucleic acid fragment encoding a biologically active portion of MP-4 includes one or more of a thioredoxin active site domain, e.g., amino acids 28–126 of SEQ ID NO:2; a transmembrane domain, e.g., amino acids 89–105, 137–161 and 182–206 of SEQ ID NO:2; a protein kinase C phosphorylation site, for example, from amino acids 92–94, 118–120, 127–129, 208–210, 220–222, and 256–258 of SEQ ID NO:2; a casein kinase II phosphorylation site, for example, from amino acids 68–71, 118–121, 127–130, 246–249, and 256–259 of SEQ ID NO:2; a tyrosine kinase phosphorylation site, for example, from amino acid 106–114, of SEQ ID NO:2; an N-myristoylation site, for example, from amino acids 20–25 and 191–196 of SEQ ID NO:2; and an amidation site, for example, from amino acid 25–28, of SEQ ID NO:2.

B. MP-4 Nucleic Acid Variants

The invention further encompasses nucleic acid molecules that differ from the nucleotide sequence shown in SEQ ID NO:1, or SEQ ID NO:3, due to degeneracy of the genetic code and thus encode the same MP-4 proteins as those encoded by the nucleotide sequence shown in SEQ ID NO:1, or SEQ ID NO:3. In another embodiment, an isolated nucleic acid molecule of the invention has a nucleotide sequence encoding a protein having an amino acid sequence shown in SEQ ID NO:2.

In addition to the MP-4 nucleotide sequences shown in SEQ ID NO:1, or SEQ ID NO:3, it will be appreciated by those skilled in the art that DNA sequence polymorphisms that lead to changes in the amino acid sequences of the MP-4 proteins may exist within a population (e.g., the human population). Such genetic polymorphism in the MP-4 genes may exist among individuals within a population due to natural allelic variation. As used herein, the terms "gene" and "recombinant gene" refer to nucleic acid molecules which include an open reading frame encoding a MP-4 protein, preferably a mammalian MP-4 protein, and can further include non-coding regulatory sequences, and introns.

Allelic variants of human MP-4 include both functional and non-functional MP-4 proteins. Functional allelic variants are naturally occurring amino acid sequence variants of the human MP-4 protein that maintain the ability to bind a MP-4 ligand and/or modulate any of the MP-4 activities described herein. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human MP-4 protein that do not have the ability to either bind a MP-4 target, e.g., an enzyme and/or modulate any of the MP-4 activities described herein.

Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human MP-4 protein. Orthologues of the human MP-4 protein are proteins that are isolated from non-human organisms and possess the same MP-4 target binding and/or modulation of signalling mechanisms of the human MP-4 protein. Orthologues of the human MP-4 protein can readily be identified as comprising an amino acid sequence that is substantially homologous to SEQ ID NO:2.

Moreover, nucleic acid molecules encoding other MP-4 family members and, thus, which have a nucleotide sequence which differs from the MP-4 sequences of SEQ ID NO:1, or SEQ ID NO:3 are intended to be within the scope of the invention. For example, another MP-4 cDNA can be identified based on the nucleotide sequence of human MP-4. Moreover, nucleic acid molecules encoding MP-4 proteins from different species, and thus which have a nucleotide sequence which differs from the MP-4 sequences of SEQ ID NO:1, or SEQ ID NO:3, are intended to be within the scope of the invention. For example, a mouse MP-4 cDNA can be identified based on the nucleotide sequence of a human MP-4.

Nucleic acid molecules corresponding to natural allelic variants and homologues of the MP-4 cDNAs of the invention can be isolated based on their homology to the MP-4 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, or SEQ ID NO:3. In other embodiment, the nucleic acid is at least 30, 50, 100, 150, 200, 250, 300, 307, 350, 400, 450, 500, 550, 600, 650, 700, 750, 800, 850, 900, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50° C., preferably at 55° C., and more preferably at 60° C. or 65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the MP-4 sequences that may exist in the population, the skilled artisan will further appreciate that changes can be introduced by mutation into the nucleotide sequences of SEQ ID NO:1, or SEQ ID NO:3, thereby leading to changes in the amino acid sequence of the encoded MP-4 proteins, without altering the functional ability of the MP-4 proteins. For example, nucleotide substitutions leading to amino acid substitutions at "non-essential" amino acid residues can be made in the sequence of SEQ ID NO:1, or SEQ ID NO:3. A "non-essential" amino acid residue is a residue that can be altered from the wild-type sequence of MP-4 (e.g., the sequence of SEQ ID NO:2) without altering the biological activity, whereas an "essential" amino acid residue is required for biological activity. For example, amino acid residues that are conserved among the MP-4 proteins of the present invention, are predicted to be particularly unamenable to alteration. Furthermore, additional amino acid residues that are conserved between the MP-4 proteins of the present invention and other members of the MP-4 thioredoxin active site families are not likely to be amenable to alteration.

Accordingly, another aspect of the invention pertains to nucleic acid molecules encoding MP-4 proteins that contain changes in amino acid residues that are not essential for activity. Such MP-4 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 60%, 65%, 70%, 75%, 80%, 85%, 90%, 95% or more homologous to SEQ ID NO:2.

An isolated nucleic acid molecule encoding a MP-4 protein homologous to the protein of SEQ ID NO:2 can be created by introducing one or more nucleotide substitutions, additions or deletions into the nucleotide sequence of SEQ ID NO:1, or SEQ ID NO:3, such that one or more amino acid substitutions, additions or deletions are introduced into the encoded protein. Mutations can be introduced into SEQ ID NO:1, or SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a MP-4 protein is preferably replaced with another amino acid residue from the same side chain family. Alternatively, in another embodiment, mutations can be introduced randomly along all or part of a MP-4 coding sequence, such as by saturation mutagenesis, and the resultant mutants can be screened for MP-4 biological activity to identify mutants that retain activity. Following mutagenesis of SEQ ID NO:1, or SEQ ID NO:3, the encoded protein can be expressed recombinantly and the activity of the protein can be determined.

In a preferred embodiment, a mutant MP-4 protein can be assayed for the ability to (1) interact with a non-MP-4 protein molecule; (2) modulate enzymatic activity, (3) modulate protein secretion, (4) prevent and/or ameliorate cellular oxidative damage, and (5) regulate free radical concentrations.

C. Antisense MP-4 Nucleic Acid Molecules

In addition to the nucleic acid molecules encoding MP-4 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MP-4 coding strand, or to only a portion thereof. In one embodiment, an antisense nucleic acid molecule is antisense to a "coding region" of the coding strand of a nucleotide sequence encoding MP-4. The term "coding region" refers to the region of the nucleotide sequence comprising codons which are translated into amino acid residues (e.g., the coding region of human MP-4 corresponds to SEQ ID NO:3). In another embodiment, the antisense nucleic acid molecule is antisense to a "noncoding region" of the coding strand of a nucleotide sequence encoding MP-4. The term "noncoding region" refers to 5' and 3' sequences which flank the coding region that are not translated into amino acids (i.e., also referred to as 5' and 3' untranslated regions).

Given the coding strand sequences encoding MP-4 disclosed herein (e.g., SEQ ID NO:3), antisense nucleic acids of the invention can be designed according to the rules of Watson and Crick base pairing. The antisense nucleic acid molecule can be complementary to the entire coding region of MP-4 mRNA, but more preferably is an oligonucleotide which is antisense to only a portion of the coding or noncoding region of MP-4 mRNA. For example, the antisense oligonucleotide can be complementary to the region surrounding the translation start site of MP-4 mRNA, e.g., an oligonucleotide having the sequence gcg cca ttt cgc cgc ttg ccc (SEQ ID NO:4) or gga ggg cgc cat ttc gcc gct tgc cca cct c (SEQ ID NO:5). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a MP-4 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual P-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

D. MP-4-Specific Ribozymes

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave MP-4 mRNA transcripts to thereby inhibit translation of MP-4 mRNA. A ribozyme having specificity for a MP-4-encoding nucleic acid can be designed based upon the nucleotide sequence of a MP-4 cDNA disclosed herein (i.e., SEQ ID NO:1, or SEQ ID NO:3. For example, a derivative of a Tetrahymena L-19 IVS RNA can be constructed in which the nucleotide sequence of the active site is complementary to the nucleotide sequence to be cleaved in a MP-4-encoding mRNA. See, e.g., Cech et al. U.S. Pat. No. 4,987,071; and Cech et al. U.S. Pat. No. 5,116,742. Alternatively, MP-4 mRNA can be used to select a catalytic RNA having a specific ribonuclease activity from a pool of RNA molecules. See, e.g., Bartel, D. and Szostak, J. W. (1993) *Science* 261:1411–1418.

Alternatively, MP-4 gene expression can be inhibited by targeting nucleotide sequences complementary to the regulatory region of the MP-4 (e.g., the MP-4 promoter and/or enhancers) to form triple helical structures that prevent transcription of the MP-4 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

E. Modified MP-4 Nucleic Acid Molecules

In yet another embodiment, the MP-4 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of MP-4 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MP-4 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of MP-4 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of MP-4 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a —stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652;

PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated MP-4 Proteins

One aspect of the invention pertains to isolated MP-4 proteins, and biologically active portions thereof, as well as polypeptide fragments suitable for use as immunogens to raise anti-MP-4 antibodies. In one embodiment, native MP-4 proteins can be isolated from cells or tissue sources by an appropriate purification scheme using standard protein purification techniques. In another embodiment, MP-4 proteins are produced by recombinant DNA techniques. Alternative to recombinant expression, a MP-4 protein or polypeptide can be synthesized chemically using standard peptide synthesis techniques.

An "isolated" or "purified" protein or biologically active portion thereof is substantially free of cellular material or other contaminating proteins from the cell or tissue source from which the MP-4 protein is derived, or substantially free from chemical precursors or other chemicals when chemically synthesized. The language "substantially free of cellular material" includes preparations of MP-4 protein in which the protein is separated from cellular components of the cells from which it is isolated or recombinantly produced. In one embodiment, the language "substantially free of cellular material" includes preparations of MP-4 protein having less than about 30% (by dry weight) of non-MP-4 protein (also referred to herein as a "contaminating protein"), more preferably less than about 20% of non-MP-4 protein, still more preferably less than about 10% of non-MP-4 protein, and most preferably less than about 5% non-MP-4 protein. When the MP-4 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of MP-4 protein in which the protein is separated from chemical precursors or other chemicals which are involved in the synthesis of the protein. In one embodiment, the language "substantially free of chemical precursors or other chemicals" includes preparations of MP-4 protein having less than about 30% (by dry weight) of chemical precursors or non-MP-4 chemicals, more preferably less than about 20% chemical precursors or non-MP-4 chemicals, still more preferably less than about 10% chemical precursors or non-MP-4 chemicals, and most preferably less than about 5% chemical precursors or non-MP-4 chemicals.

As used herein, a "biologically active portion" of a MP-4 protein includes a fragment of a MP-4 protein which participates in an interaction between a MP-4 molecule and a non-MP-4 molecule. Biologically active portions of a MP-4 protein include peptides comprising amino acid sequences sufficiently homologous to or derived from the amino acid sequence of the MP-4 protein, e.g., the amino acid sequence shown in SEQ ID NO:2, which include less amino acids than the full length MP-4 proteins, and exhibit at least one activity of a MP-4 protein. Typically, biologically active portions comprise a domain or motif with at least one activity of the MP-4 protein, e.g., regulating reduction of a disulfide bond. A biologically active portion of a MP-4 protein can be a polypeptide which is, for example, 10, 25, 50, 100, 200 or 250 amino acids in length. Biologically active portions of a MP-4 protein can be used as targets for developing agents which modulate a thioredoxin family active site mediated activity.

In one embodiment, a biologically active portion of a MP-4 protein comprises at least one transmembrane domain. In another embodiment, a biologically active portion of a MP-4 protein comprises at least one thioredoxin family active site domain. In yet another embodiment a biologically active portion of a MP-4 protein comprises at least one transmembrane domain and at least one thioredoxin family active site domain.

It is to be understood that a preferred biologically active portion of a MP-4 protein of the present invention may contain at least one of the above-identified structural domains. A more preferred biologically active portion of a MP-4 protein may contain at least two of the above-identified structural domains. Moreover, other biologically active portions, in which other regions of the protein are deleted, can be prepared by recombinant techniques and evaluated for one or more of the functional activities of a native MP-4 protein.

In a preferred embodiment, the MP-4 protein has an amino acid sequence shown in SEQ ID NO:2. In other embodiments, the MP-4 protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the MP-4 protein is a protein which comprises an amino acid sequence at least about 60%, 65%, 70%, 75%, 80%, 85%, 90%, 95% or more homologous to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the MP-4 amino acid sequence of SEQ ID NO:2, having 280 amino acid residues, at least 80, preferably at least 100, more preferably at least 140, even more preferably at least 180, and even more preferably at least 200, 220, 240, or 250 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at ttp://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to MP-4 nucleic acid molecules of the invention. BLAST protein searches can be performed with the XBLAST program, score=50, wordlength=3 to obtain amino acid sequences homologous to MP-4 protein molecules of the invention. To obtain gapped alignments for comparison purposes, Gapped BLAST can be utilized as described in Altschul et al., (1997) *Nucleic Acids Res.* 25(17) :3389–3402. When utilizing BLAST and Gapped BLAST programs, the default parameters of the respective programs (e.g., XBLAST and NBLAST) can be used. See http://www.ncbi.nlm.nih.gov.

A. MP-4 Chimeric or Fusion Proteins

The invention also provides MP-4 chimeric or fusion proteins. As used herein, a MP-4 "chimeric protein" or "fusion protein" comprises a MP-4 polypeptide operatively linked to a non-MP-4 polypeptide. An "MP-4 polypeptide" refers to a polypeptide having an amino acid sequence corresponding to MP-4, whereas a "non-MP-4 polypeptide" refers to a polypeptide having an amino acid sequence corresponding to a protein which is not substantially homologous to the MP-4 protein, e.g., a protein which is different from the MP-4 protein and which is derived from the same or a different organism. Within a MP-4 fusion protein the MP-4 polypeptide can correspond to all or a portion of a MP-4 protein. In a preferred embodiment, a MP-4 fusion protein comprises at least one biologically active portion of a MP-4 protein. In another preferred embodiment, a MP-4 fusion protein comprises at least two biologically active portions of a MP-4 protein. Within the fusion protein, the term "operatively linked" is intended to indicate that the MP-4 polypeptide and the non-MP-4 polypeptide are fused in-frame to each other. The non-MP-4 polypeptide can be fused to the N-terminus or C-terminus of the MP-4 polypeptide.

For example, in one embodiment, the fusion protein is a GST-MP-4 fusion protein in which the MP-4 sequences are fused to the C-terminus of the GST sequences. Such fusion proteins can facilitate the purification of recombinant MP-4.

In another embodiment, the fusion protein is a MP-4 protein containing a heterologous signal sequence at its N-terminus. In certain host cells (e.g., mammalian host cells), expression and/or secretion of MP-4 can be increased through use of a heterologous signal sequence.

The MP-4 fusion proteins of the invention can be incorporated into pharmaceutical compositions and administered to a subject in vivo. The MP-4 fusion proteins can be used to affect the bioavailability of a MP-4 substrate. Use of MP-4 fusion proteins may be useful therapeutically for the treatment of a disorders, e.g., a cardiovascular disorder such as atherosclerosis, ischaemia reperfusion injury, cardiac hypertrophy, hypertension, coronary artery disease, myocardial infarction, arrythmia, cardiomyopathies, and congestive heart failure.

Moreover, the MP-4-fusion proteins of the invention can be used as immunogens to produce anti-MP-4 antibodies in a subject, to purify MP-4 ligands and in screening assays to identify molecules which inhibit the interaction of MP-4 with a MP-4 substrate.

Preferably, a MP-4 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MP-4-encoding nucleic acid can be cloned into such an expression vector such that the fusion moiety is linked in-frame to the MP-4 protein.

B. Variants of MP-4 Proteins

The present invention also pertains to variants of the MP-4 proteins which function as either MP-4 agonists (mimetics) or as MP-4 antagonists. Variants of the MP-4 proteins can be generated by mutagenesis, e.g., discrete point mutation or truncation of a MP-4 protein. An agonist of the MP-4 proteins can retain substantially the same, or a subset, of the biological activities of the naturally occurring form of a MP-4 protein. An antagonist of a MP-4 protein can inhibit one or more of the activities of the naturally occurring form of the MP-4 protein by, for example, competitively modulating a thioredoxin active site mediated activity of a MP-4 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MP-4 protein.

In one embodiment, variants of a MP-4 protein which function as either MP-4 agonists (mimetics) or as MP-4 antagonists can be identified by screening combinatorial libraries of mutants, e.g., truncation mutants, of a MP-4 protein for MP-4 protein agonist or antagonist activity. In one embodiment, a variegated library of MP-4 variants is generated by combinatorial mutagenesis at the nucleic acid level and is encoded by a variegated gene library. A variegated library of MP-4 variants can be produced by, for example, enzymatically ligating a mixture of synthetic oligonucleotides into gene sequences such that a degenerate set of potential MP-4 sequences is expressible as individual polypeptides, or alternatively, as a set of larger fusion proteins (e.g., for phage display) containing the set of MP-4 sequences therein. There are a variety of methods which can be used to produce libraries of potential MP-4 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MP-4 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a MP-4 protein coding sequence can be used to generate a variegated population of MP-4 fragments for screening and subsequent selection of variants of a MP-4 protein. In one embodiment, a library of coding sequence fragments can be generated by treating a double stranded PCR fragment of an MP-4 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MP-4 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MP-4 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify MP-4 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated MP-4 library. For example, a library of expression vectors can be transfected into a cell line which ordinarily synthesizes MP-4. The transfected cells are then cultured such that MP-4 and a particular mutant MP-4 are expressed and the effect of expression of the mutant on MP-4 activity in the cells can be detected, e.g., by any of a number of enzymatic assays or by detecting the enzymatic activity. Plasmid DNA can then be recovered from the cells which score for inhibition, or alternatively, potentiation of MP-. 4 activity, and the individual clones further characterized.

III. Anti-MP-4 Antibodies

An isolated MP-4 protein, or a portion or fragment thereof, can be used as an immunogen to generate antibodies that bind MP-4 using standard techniques for polyclonal and monoclonal antibody preparation. A full-length MP-4 protein can be used or, alternatively, the invention provides antigenic peptide fragments of MP-4 for use as immunogens. The antigenic peptide of MP-4 comprises at least 8 amino acid residues of the amino acid sequence shown in SEQ ID NO:2 and encompasses an epitope of MP-4 such that an antibody raised against the peptide forms a specific immune complex with MP-4. Preferably, the antigenic peptide comprises at least 10 amino acid residues, more preferably at least 15 amino acid residues, even more preferably at least 20 amino acid residues, and most preferably at least 30 amino acid residues.

Figure 4:
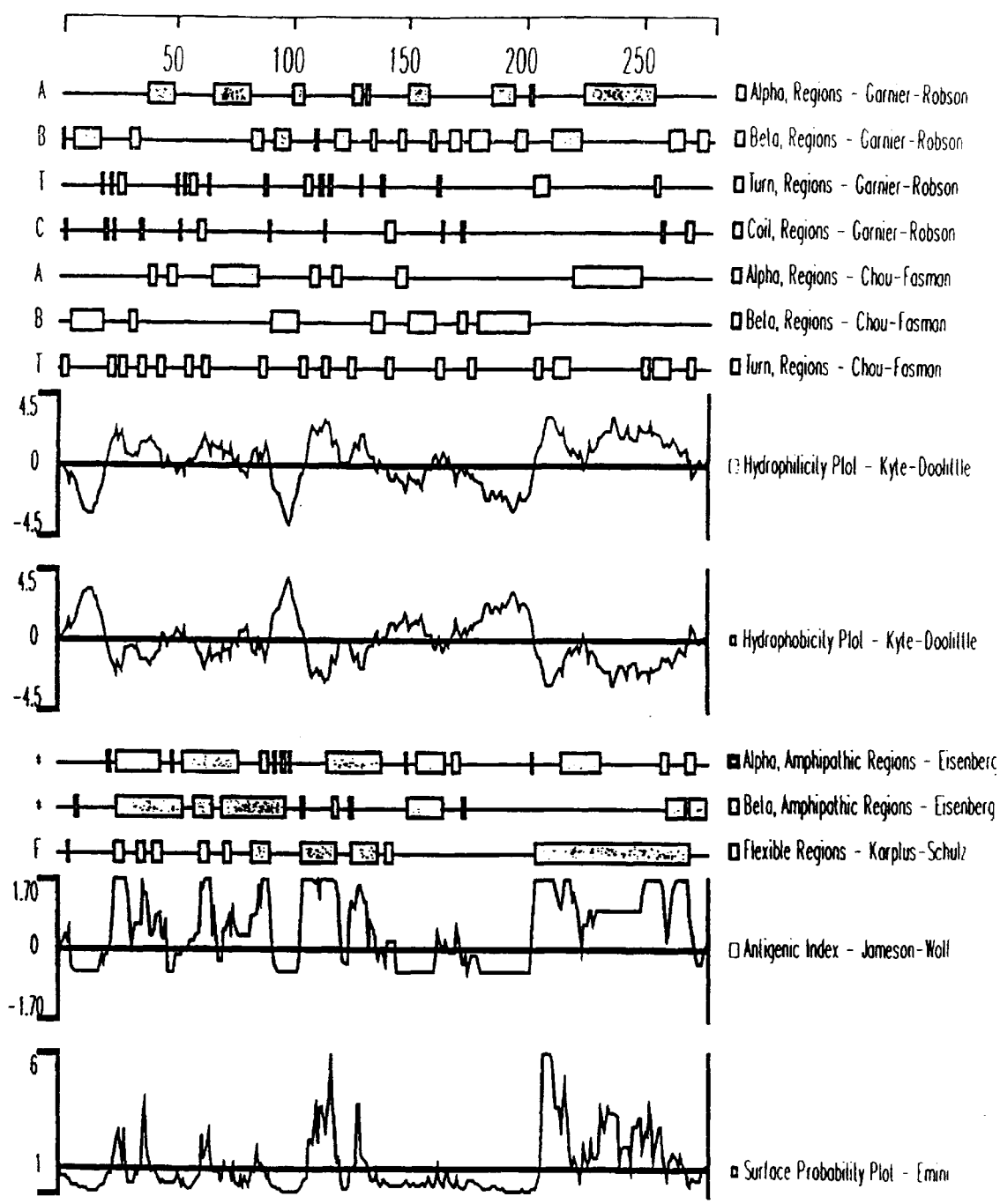
FIG. 4 shows a structural, hydrophobicity, and antigenicity analysis of the human MP-4 amino acid sequence (SEQ ID NO:2).

Preferred epitopes encompassed by the antigenic peptide are regions of MP-4 that are located on the surface of the protein, e.g., hydrophilic regions, as well as regions with high antigenicity (see, for example, FIG. 4). For example, an Emini surface probability analysis of the human MP-4 protein sequence (FIG. 4) indicates that the regions between, e.g., amino acids 108 and 121, between amino acids 208 and 223, and between amino acids 226 and 251 of SEQ ID NO:2 are have a particularly high probability of being localized to the surface of the MP-4 protein and are thus likely to constitute surface residues useful for targeting antibody production.

A MP-4 immunogen typically is used to prepare antibodies by immunizing a suitable subject, (e.g., rabbit, goat, mouse or other mammal) with the immunogen. An appropriate immunogenic preparation can contain, for example, recombinantly expressed MP-4 protein or a chemically synthesized MP-4 polypeptide. The preparation can further include an adjuvant, such as Freund's complete or incomplete adjuvant, or similar immunostimulatory agent. Immunization of a suitable subject with an immunogenic MP-4 preparation induces a polyclonal anti-MP-4 antibody response.

Accordingly, another aspect of the invention pertains to anti-MP-4 antibodies. The term "antibody" as used herein refers to immunoglobulin molecules and immunologically active portions of immunoglobulin molecules, i.e., molecules that contain an antigen binding site which specifically binds (immunoreacts with) an antigen. such as MP-4. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind MP-4. The term "monoclonal antibody" or "monoclonal antibody composition", as used herein, refers to a population of antibody molecules that contain only one species of an antigen binding site capable of immunoreacting with a particular epitope of MP-4. A monoclonal antibody composition thus typically displays a single binding affinity for a particular MP-4 protein with which it immunoreacts.

Polyclonal anti-MP-4 antibodies can be prepared as described above by immunizing a suitable subject with a MP-4 immunogen. The anti-MP-4 antibody titer ina the immunized subject can be monitored over time by standard techniques, such as with an enzyme linked immunosorbent assay (ELISA) using immobilized MP-4. If desired, the antibody molecules directed against MP-4 can be isolated from the mammal (e.g., from the blood) and further purified by well known techniques, such as protein A chromatography to obtain the IgG fraction. At an appropriate time after immunization, e.g., when the anti-MP-4 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological* Analyses, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a MP-4 immunogen as described above, and the culture supernatants of the resulting hybridoma cells are screened to identify a hybridoma producing a monoclonal antibody that binds MP-4.

Any of the many well known protocols used for fusing lymphocytes and immortalized cell lines can be applied for the purpose of generating an anti-MP-4 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind MP-4, e.g., using a standard ELISA assay.

Alternative to preparing monoclonal antibody-secreting hybridomas, a monoclonal anti-MP-4 antibody can be identified and isolated by screening a recombinant combinatorial immunoglobulin library (e.g., an antibody phage display library) with MP-4 to thereby isolate immunoglobulin library members that bind MP-4. Kits for generating and screening phage display libraries are commercially available (e.g., the Pharmacia *Recombinant Phage Antibody System*, Catalog No. 27-9400-01; and the Stratagene SurgZAP™Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-MP-4 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in. Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-MP-4 antibody (e.g., monoclonal antibody) can be used to isolate MP-4 by standard techniques, such as affinity chromatography or immunoprecipitation. An anti-MP-4 antibody can facilitate the purification of natural MP-4 from cells and of recombinantly produced MP-4 expressed in host cells. Moreover, an anti-MP-4 antibody can be used to detect MP-4 protein (e.g., in a cellular lysate or cell supernatant) in order to evaluate the abundance and pattern of expression of the MP-4 protein. Anti-MP-4 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

IV. Recombinant Expression Vectors and Host Cells

Another aspect of the invention pertains to vectors, preferably expression vectors, containing a nucleic acid encoding a MP-4 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., MP-4 proteins, mutant forms of MP-4 proteins, fusion proteins, and the like).

The recombinant expression vectors of the invention can be designed for expression of MP-4 proteins in prokaryotic or eukaryotic cells. For example, MP-4 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase Typical fusion expression vectors include pGEX (Pharmacia Biotech Inc; Smith, D. B. and Johnson, K. S. (1988) *Gene* 67:31–40), pMAL (New England Biolabs, Beverly, Mass.,) and pRIT5 (Pharmacia, Piscataway, N.J.) which fuse glutathione S-transferase (GST), maltose E binding protein, or protein A, respectively, to the target recombinant protein.

Purified fusion proteins can be utilized in MP-4 activity assays, (e.g., direct assays or competitive assays described in detail below), or to generate antibodies specific for MP-4 proteins, for example. In a preferred embodiment, a MP-4 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the MP-4 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, MP-4 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the oc-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MP-4 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a MP-4 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a MP-4 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a MP-4 protein. Accordingly, the invention further provides methods for producing a MP-4 protein using the host cells of the invention. In one embodiment, the method comprises culturing the host cell of invention (into which a recombinant expression vector encoding a MP-4 protein has been introduced) in a suitable medium such that a MP-4 protein is produced. In another embodiment, the method further comprises isolating a MP-4 protein from the medium or the host cell.

The host cells of the invention can also be used to produce non-human transgenic animals. For example, in one embodiment, a host cell of the invention is a fertilized oocyte or an embryonic stem cell into which MP-4-coding sequences have been introduced. Such host cells can then be used to create non-human transgenic animals in which exogenous MP-4 sequences have been introduced into their genome or homologous recombinant animals in which endogenous MP-4 sequences have been altered. Such animals are useful for studying the function and/or activity of a MP-4 and for identifying and/or evaluating modulators of MP-4 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous MP-4 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a MP-4-encoding nucleic acid into the male pronuclei of a fertilized oocyte, e.g., by microinjection, retroviral infection, and allowing the oocyte to develop in a pseudopregnant female foster animal. The MP-4 cDNA sequence of SEQ ID NO:1 can be be introduced as a transgene into the genome of a non-human animal. Alternatively, a nonhuman homologue of a human MP-4 gene, such as a mouse or rat MP-4 gene, can be used as a transgene. Alternatively, a MP-4 gene homologue, such as another MP-4 thioredoxin active site family member, can be isolated based on hybridization to the MP-4 cDNA sequences of SEQ ID NO:1, or SEQ ID NO:3 (described further in subsection I above) and used as a transgene. Intronic sequences and polyadenylation signals can also be included in the transgene to increase the efficiency of expression of the transgene. A tissue-specific regulatory sequence(s) can be operably linked to a MP.-4 transgene to direct expression of a MP-4 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a MP-4 transgene in its genome and/or expression of MP-4 mRNA in tissues or cells of the animals. A transgenic founder animal can then be used to breed additional animals carrying the transgene. Moreover, transgenic animals carrying a transgene encoding a MP-4 protein can further be bred to other transgenic animals carrying other transgenes.

To create a homologous recombinant animal, a vector is prepared which contains at least a portion of a MP-4 gene into which a deletion, addition or substitution has been introduced to thereby alter, e.g., functionally disrupt, the MP-4 gene. The MP-4 gene can be a human gene (e.g., the cDNA of SEQ ID NO:3), but more preferably, is a non-human homologue of a human MP-4 gene (e.g., a cDNA isolated by stringent hybridization with the nucleotide sequence of SEQ ID NO:1). For example, a mouse MP-4 gene can be used to construct a homologous recombination vector suitable for altering an endogenous MP-4 gene in the mouse genome. In a preferred embodiment, the vector is designed such that, upon homologous recombination, the endogenous MP-4 gene is functionally disrupted (i.e., no longer encodes a functional protein; also referred. to as a "knock out" vector). Alternatively, the vector can be designed such that, upon homologous recombination, the endogenous MP-4 gene is mutated or otherwise altered but still encodes functional protein (e.g., the upstream regulatory region can be altered to thereby alter the expression of the endogenous MP-4 protein). In the homologous recombination vector, the altered portion of the MP-4 gene is flanked at its 5' and 3' ends by additional nucleic acid sequence of the MP-4 gene to allow for homologous recombination to occur between the exogenous MP-4 gene carried by the vector and an endogenous MP-4 gene in an embryonic stem cell. The additional flanking MP-4 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced MP-4 gene has homologously recombined with the endogenous MP-4 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

The MP-4 nucleic acid molecules, fragments of MP-4 proteins, and anti-MP-4 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a MP-4 protein or an anti-MP-4 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint. methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Depending on the type and severity of the disease, about 1 μg/kg to 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy can be monitored by standard techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a MP-4 protein of the invention has one or more of the following activities: (1) it can modulate enzymatic activity, (2) it can modulate protein processing and/or folding, (3) it can modulate protein secretion, (4) it can modulate protein disulfide isomerization, (5) it can catalyze the oxidation of a thiol group and/or the reduction of a disulfide bond of a target protein or polypeptide, e.g., an enzyme, (6) it can sense and/or transmit the redox state in a cell, (7) prevent and/or ameliorate cellular oxidative damage, (8) it can regulate free radical concentrations, and (9) it can modulate cardiovascular activities, and, thus, can be used to, for example, (1) modulate enzymatic activity, (2) modulate protein processing and/or folding, (3) modulate protein secretion, (4) modulate protein disulfide isomerization, (5) catalyze the oxidation of a thiol group and/or the reduction of a disulfide bond of a target protein or polypeptide, e.g., an enzyme, (6) sense and/or transmit the redox state in a cell, (7) prevent and/or ameliorate cellular oxidative damage, (8) regulate free radical concentrations, and (9) modulate cardiovascular activities.

The isolated nucleic acid molecules of the invention can be used, for example, to express MP-4 protein (e.g., via a recombinant expression vector in a host cell in gene therapy applications), to detect MP-4 mRNA (e.g., in a biological sample) or a genetic alteration in a MP-4 gene, and to modulate MP-4 activity, as described further below. The MP-4 proteins can be used to treat disorders characterized by insufficient or excessive production of a MP-4 substrate or production of MP-4 inhibitors. In addition., the MP-4 proteins can be used to screen for naturally occurring MP-4 substrates, to screen for drugs or compounds which modulate MP-4 activity, as well as to treat disorders characterized by insufficient or excessive production of MP-4 protein or production of MP-4 protein forms which have decreased or aberrant activity compared to MP-4 wild type protein (e.g., a cardiovascular disorder, e.g., atherosclerosis, ischaemia reperfusion injury, cardiac hypertrophy, hypertension, coronary artery disease, myocardial infarction, arrythmia, cardiomyopathies, and congestive heart failure; a connective tissue disorder, e.g., Ehlers-Danlos Syndrome; or a hepatic disorder, e.g., alcoholic liver disease, liver cirrhosis, liver cancer). Moreover, the anti-MP-4 antibodies of the invention can be used to detect and isolate MP-4 proteins, regulate the bioavailability of MP-4 proteins, and modulate MP-4 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to MP-4 proteins, have a stimulatory or inhibitory effect on, for example, MP-4 expression or MP-4 activity, or have a stimulatory or inhibitory effect on, for example, the expression or activity of MP-4 substrate.

In one embodiment, the invention provides assays for screening candidate or test compounds which are substrates of a MP-4 protein or polypeptide or biologically active portion thereof. In another embodiment, the invention provides assays for screening candidate or test compounds which bind to or modulate the activity of a MP-4 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner USP 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladnersupra.).

In one embodiment, an assay is a cell-based assay in which a cell which expresses a MP-4 protein or biologically active portion thereof is contacted with a test compound and the ability of the test compound to modulate MP-4 activity is determined. Determining the ability of the test compound to modulate MP-4 activity can be accomplished by monitoring, for example, the release of a neurotransmitter form a cell which expresses MP-4. The cell, for example, can be of mammalian origin. Determining the ability of the test compound to modulate the ability of MP-4 to bind to a substrate can be accomplished, for example, by coupling the MP-4 substrate with a radioisotope or enzymatic label such that binding of the MP-4 substrate to MP-4 can be determined by detecting the labeled MP-4 substrate in a complex. For example, compounds (e.g., MP-4 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., MP-4 substrate) to interact with MP-4 without the labeling of any of the interactants. For example, a microphysiometer can be used to detect the interaction of a compound with MP-4 without the labeling of either the compound or the MP-4.

McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and MP-4.

In another embodiment, an assay is a cell-based assay comprising contacting a cell expressing a MP-4 target molecule (e.g., a MP-4 substrate) with a test compound and determining the ability of the test compound to modulate (e.g. stimulate or inhibit) the activity of the MP-4 target molecule. Determining the ability of the test compound to modulate the activity of a MP-4 target molecule can be accomplished, for example, by determining the ability of the MP-4 protein to bind to or interact with the MP-4 target molecule.

Determining the ability of the MP-4 protein or a biologically active fragment thereof, to bind to or interact with a MP-4 target molecule can be accomplished by one of the methods described above for determining direct binding. In a preferred embodiment, determining the ability of the MP-4 protein to bind to or interact with a MP-4 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/ enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a MP-4 protein or biologically active portion thereof is contacted with a test compound and the ability of the test compound to bind to the MP-4 protein or biologically active portion thereof is determined. Preferred biologically active portions of the MP-4 proteins to be used in assays of the present invention include fragments which participate in interactions with non-MP-4 molecules, e.g., an enzyme, or fragments with high surface probability scores (see, for example, FIG. 4). Binding of the test compound to the MP-4 protein can be determined either directly or indirectly as described above. In a preferred embodiment, the assay includes contacting the MP-4 protein or biologically active portion thereof with a known compound which binds MP-4 to form an assay mixture, contacting the assay mixture with a test compound, and determining the ability of the test compound to interact with a MP-4 protein, wherein determining the ability of the test compound to interact with a MP-4 protein comprises determining the ability of the test compound to preferentially bind to MP-4 or biologically active portion thereof as compared to the known compound.

In another embodiment, the assay is a cell-free assay in which a MP-4 protein or -biologically active portion thereof is contacted with a test compound and the ability of the test compound to modulate (e.g., stimulate or inhibit) the activity of the MP-4 protein or biologically active portion thereof is determined. Determining the ability of the test compound to modulate the activity of a MP-4 protein can be accomplished, for example, by determining the ability of the MP-4 protein to bind to a MP-4 target molecule by one of the methods described above for determining direct binding. Determining the ability of the MP-4 protein to bind to a MP-4 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr.*

*Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a MP-4 protein can be accomplished by determining the ability of the MP-4 protein to further modulate the activity of a downstream effector of a MP-4 target molecule. For example, the activity of the effector molecule on an appropriate target can be determined or the binding of the effector to an appropriate target can be determined as previously described.

In yet another embodiment, the cell-free assay involves contacting a MP-4 protein or biologically active portion thereof with a known compound which binds the MP-4 protein to form an assay mixture, contacting the assay mixture with a test compound, and determining the ability of the test compound to interact with the MP-4 protein, wherein determining the ability of the test compound to interact with the MP-4 protein comprises determining the ability of the MP-4 protein to preferentially bind to or modulate the activity of a MP-4 target molecule.

The cell-free assays of the present invention are amenable to use of both soluble and/or membrane-bound forms of isolated proteins (e.g., MP-4 proteins or biologically active portions thereof). In the case of cell-free assays in which a membrane-bound form an isolated protein is used (e.g., a thioredoxin active site protein) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either MP-4 or its target molecule to facilitate separation of complexed from uncomplexed forms of one or both of the proteins, as well as to accommodate automation of the assay. Binding of a test compound to a MP-4 protein, or interaction of a MP-4 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/MP-4 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or MP-4 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of MP-4 binding or activity determined using standard techniques.

Other techniques for immobilizing proteins on matrices can also be used in the screening assays of the invention. For example, either a MP-4 protein or a MP-4 target molecule can be immobilized utilizing conjugation of biotin and streptavidin. Biotinylated MP-4 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with MP-4 protein or target molecules but which do not interfere with binding of the MP-4 protein to its target molecule can be derivatized to the wells of the plate, and unbound target or MP-4 protein trapped in the wells by antibody conjugation. Methods for detecting such complexes, in addition to those described above for the GST-immobilized complexes, include immunodetection of complexes using antibodies reactive with the MP-4 protein or target molecule, as well as enzyme-linked assays which rely on detecting an enzymatic activity associated with the MP-4 protein or target molecule.

In another embodiment, modulators of MP-4 expression are identified in a method wherein a cell is contacted with a candidate compound and the expression of MP-4 mRNA or protein in the cell is determined. The level of expression of MP-4 mRNA or protein in the presence of the candidate compound is compared to the level of expression of MP-4 mRNA or protein in the absence of the candidate compound. The candidate compound can then be identified as a modulator of MP-4 expression based on this comparison. For example, when expression of MP-4 mRNA or protein is greater (statistically significantly greater) in the presence of the candidate compound than in its absence, the candidate compound is identified as a stimulator of MP-4 mRNA or protein expression. Alternatively, when expression of MP-4 mRNA or protein is less (statistically significantly less) in the presence of the candidate compound than in its absence, the candidate compound is identified as an inhibitor of MP-4 mRNA or protein expression. The level of MP-4 mRNA or protein expression in the cells can be determined by methods described herein for detecting MP-4 mRNA or protein.

In yet another aspect of the invention, the MP-4 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with MP-4 ("MP-4-binding proteins" or "MP-4-bp") and are involved in -MP-4 activity. Such MP-4-binding proteins are also likely to be involved in the propagation of signals by the MP-4 proteins or MP-4 targets as, for example, downstream elements of a MP-4-mediated signaling pathway. Alternatively, such MP-4-binding proteins are likely to be MP-4 inhibitors.

The two-hybrid system is based on the modular nature of most transcription factors, which consist of separable DNA-binding and activation domains. Briefly, the assay utilizes two different DNA constructs. In one construct, the gene that codes for a MP-4 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a MP-4-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MP-4 protein.

This invention further pertains to novel agents identified by the above-described screening assays. Accordingly, it is within the scope of this invention to further use an agent identified as described herein in an appropriate animal model. For example, an agent identified as described herein (e.g., a MP-4 modulating agent, an antisense MP-4 nucleic acid molecule, a MP-4-specific antibody, or a MP-4-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the MP-4 nucleotide sequences, described herein, can be used to map the location of the MP-4 genes on a chromosome. The mapping of the MP-4 sequences to chromosomes is an important first step in correlating these sequences with genes associated with disease.

Briefly, MP-4 genes can be mapped to chromosomes by preparing PCR primers (preferably 15–25 bp in length) from the MP-4 nucleotide sequences. Computer analysis of the MP-4 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the MP-4 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the MP-4 nucleotide sequences to design oligonucleotide primers, sublocalization can be achieved with panels of fragments from specific chromosomes. Other mapping strategies which can similarly be used to map a MP-4 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the MP-4 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The MP-4 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the MP-4 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The MP-4 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from MP-4 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial MP-4 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the MP-4 nucleotide sequences or portions thereof, e.g., fragments derived from the noncoding regions of SEQ ID NO:1, having a length of at least 20 bases, preferably at least 30 bases.

The MP-4 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such MP-4 probes can be used to identify tissue by species and/or by organ type.

In a similar fashion, these reagents, e.g., MP-4 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically.

Accordingly, one aspect of the present invention relates to diagnostic assays for determining MP-4 protein and/or nucleic acid expression as well as MP-4 activity, in the context of a biological sample (e.g., blood, serum, cells, tissue) to thereby determine whether an individual is afflicted with a disease or disorder, or is at risk of developing a disorder, associated with aberrant MP-4 expression or activity. The invention also provides for prognostic (or predictive) assays for determining whether an individual is at risk of developing a disorder associated with MP-4 protein, nucleic acid expression or activity. For example, mutations in a MP-4 gene can be assayed in a biological sample. Such assays can be used for prognostic or predictive purpose to thereby phophylactically treat an individual prior to the onset of a disorder characterized by or associated with MP-4 protein, nucleic acid expression or activity.

Another aspect of the invention pertains to monitoring the influence of agents (e.g., drugs, compounds) on the expression or activity of MP-4 in clinical trials.

These and other agents are described in further detail in the following sections.

1. Diagnostic Assays

An exemplary method for detecting the presence or absence of MP-4 protein or nucleic acid in a biological sample involves obtaining a biological sample from a test subject and contacting the biological sample with a compound or an agent capable of detecting MP-4 protein or nucleic acid (e.g., mRNA, genomic DNA) that encodes MP-4 protein such that the presence of MP-4 protein or nucleic acid is detected in the biological sample. A preferred agent for detecting MP-4 mRNA or genomic DNA is a labeled nucleic acid probe capable of hybridizing to MP-4 mRNA or genomic DNA.

The nucleic acid probe can be, for example, a full-length MP-4 nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to MP-4 mRNA or genomic DNA. Other suitable probes for use in the diagnostic assays of the invention are described herein.

A preferred agent for detecting MP-4 protein is an antibody capable of binding to MP-4 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect MP-4 mRNA, protein, or genomic DNA in a biological sample in vitro as well as in vivo. For example, in vitro techniques for detection of MP-4 mRNA include Northern hybridizations and in situ hybridizations. In vitro techniques for detection of MP-4 protein include enzyme linked immunosorbent assays (ELISAs), Western blots, immunoprecipitations and immunofluorescence. In vitro techniques for detection of MP-4 genomic DNA include Southern hybridizations. Furthermore, in vivo techniques for detection of MP-4 protein include introducing into a subject a labeled anti-MP-4 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting MP-4 protein, mRNA, or genomic DNA, such that the presence of MP-4 protein, mRNA or genomic DNA is detected in the biological sample, and comparing the presence of MP-4 protein, mRNA or genomic DNA in the control sample with the presence of MP-4 protein, mRNA or genomic DNA in the test sample.

The invention also encompasses kits for detecting the presence of MP-4 in a biological sample. For example, the kit can comprise a labeled compound or agent capable of detecting MP-4 protein or mRNA in a biological sample; means for determining the amount of MP-4 in the sample; and means for comparing the amount of MP-4 in the sample with a standard. The compound or agent can be packaged in a suitable container. The kit can further comprise instructions for using the kit to detect MP-4 protein or nucleic acid.

2. Prognostic Assays

The diagnostic methods described herein can furthermore be utilized to identify subjects having or at risk of developing a disease or disorder associated with aberrant MP-4 expression or activity. For example, the assays described herein, such as the preceding diagnostic assays or the following assays, can be utilized to identify a subject having or at risk of developing a disorder associated with a misregulation in MP-4 protein activity or nucleic acid expression, such as a cardiovascular, hepatic or connective tissue disorder. Alternatively, the prognostic assays can be utilized to identify a subject having or at risk for developing a disorder associated with a misregulation in MP-4 protein activity or nucleic acid expression, such as a cardiovascular, hepatic or connective tissue disorder. Thus, the present invention provides a method for identifying a disease or disorder associated with aberrant MP-4 expression or activity in which a test sample is obtained from a subject and MP-4 protein or nucleic acid (e.g., mRNA or genomic DNA) is detected, wherein the presence of MP-4 protein or nucleic acid is diagnostic for a subject having or at risk of developing a disease or disorder associated with aberrant MP-4 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant MP-4 expression or activity. For example, such methods can be used to determine whether a subject can be effectively treated with an agent for a cardiovascular, hepatic or connective tissue disorder. Thus, the present invention provides methods for determining whether a subject can be effectively treated with an agent for a disorder associated with aberrant MP-4 expression or activity in which a test sample is obtained and MP-4 protein or nucleic acid expression or activity is detected (e.g., wherein the abundance of MP-4 protein or nucleic acid expression or activity is diagnostic for a subject that can be administered the agent to treat a disorder associated with aberrant MP-4 expression or activity).

The methods of the invention can also be used to detect genetic alterations in a MP-4 gene, thereby determining if a subject with the altered gene is at risk for a disorder characterized by misregulation in MP-4 protein activity or nucleic acid expression, such as a cardiovascular, hepatic or connective tissue disorder. In preferred embodiments, the methods include detecting, in a sample of cells from the subject, the presence or absence of a genetic alteration characterized by at least one of an alteration affecting the integrity of a gene encoding a MP-4-protein, or the misexpression of the MP-4 gene. For example, such genetic alterations can be detected by ascertaining the existence of at least one of 1) a deletion of one or more nucleotides from an MP-4 gene; 2) an addition of one or more nucleotides to an MP-4 gene; 3) a substitution of one or more nucleotides of an MP-4 gene, 4) a chromosomal rearrangement of an MP-4 gene; 5) an alteration in the level of a messenger RNA transcript of an MP-4 gene, 6) aberrant modification of an MP-4 gene, such as of the methylation pattern of the genomic DNA, 7) the presence of a non-wild type splicing pattern of a messenger RNA transcript of an MP-4 gene, 8) a non-wild type level of an MP-4-protein, 9) allelic loss of an MP-4 gene, and 10) inappropriate post-translational modification of an MP-4-protein. As described herein, there are a large number of assays known in the art which can be used for detecting alterations in a MP-4 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the MP-4-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a MP-4 gene under conditions such that hybridization and amplification of the MP-4-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a MP-4 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MP-4 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in MP-4 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MP-4 gene and detect mutations by comparing the sequence of the sample MP-4 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the MP-4 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type MP-4 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in MP-4 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a MP-4 sequence, e.g., a wild-type MP-4 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in MP-4 genes. For example, single strand conformation polymorphism (SSCP) may be used to detect differences in electrophoretic mobility between mutant and wild type nucleic acids (Orita et al. (1989) *Proc. Natl. Acad. Sci. USA:* 86:2766, see also Cotton (1993) *Mutat. Res.* 285:125–144; and Hayashi (1992) *Genet. Anal. Tech. Appl.* 9:73–79). Single-stranded DNA fragments of sample and control MP-4 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a MP-4 gene.

Furthermore, any cell type or tissue in which MP-4 is expressed may be utilized in the prognostic assays described herein.

3. Monitoring of Effects During Clinical Trials

Monitoring the influence of agents (e.g., drugs) on the expression or activity of a MP-4 protein (e.g., the modulation of membrane excitability or resting potential) can be applied not only in basic drug screening, but also in clinical trials. For example, the effectiveness of an agent determined by a screening assay as described herein to increase MP-4 gene expression, protein levels, or upregulate MP-4 activity, can be monitored in clinical trials of subjects exhibiting decreased MP-4 gene expression, protein levels, or down-regulated MP-4 activity. Alternatively, the effectiveness of an agent determined by a screening assay to decrease MP-4 gene expression, protein levels, or downregulate MP-4 activity, can be monitored in clinical trials of subjects exhibiting increased MP-4 gene expression, protein levels, or upregulated MP-4 activity. In such clinical trials, the expression or activity of a MP-4 gene, and preferably, other genes that have been implicated in, for example, a thioredoxin active site associated disorder can be used as a "read out" or markers of the phenotype of a particular cell.

For example, and not by way of limitation, genes, including MP-4, that are modulated in cells by treatment with an agent (e.g., compound, drug or small molecule) which modulates MP-4 activity (e.g., identified in a screening assay as described herein) can be identified. Thus, to study the effect of agents on thioredoxin active site associated disorders, for example, in a clinical trial, cells can be isolated and RNA prepared and analyzed for the levels of expression of MP-4 and other genes implicated in the thioredoxin active site associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of MP-4 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a MP-4 protein, mRNA, or genomic DNA in the preadministration sample; (iii) obtaining one or more post-administration samples from the subject; (iv) detecting the level of expression or activity of the MP-4 protein, mRNA, or genomic DNA in the post-administration samples; (v) comparing the level of expression or activity of the MP-4 protein, mRNA, or genomic DNA in the pre-administration sample with the MP-4 protein, mRNA, or genomic DNA in the post administration sample or samples; and (vi) altering the administration of the agent to the subject accordingly. For example, increased administration of the agent may be desirable to increase the expression or activity of MP-4 to higher levels than detected, i.e., to increase the effectiveness of the agent. Alternatively, decreased administration of the agent may be desirable to decrease expression or activity of MP-4 to lower levels than detected, i.e. to decrease the effectiveness of the agent. According to such an embodiment, MP-4 expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant MP-4 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MP-4 molecules of the present invention or MP-4 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant MP-4 expression or activity, by administering to the subject a MP-4 or an agent which modulates MP-4 expression or at least one MP-4 activity. Subjects at risk for a disease which is caused or contributed to by aberrant MP-4 expression or activity can be identified by, for example, any or a combination of diagnostic or prognostic assays as described herein. Administration of a prophylactic agent can occur prior to the manifestation of symptoms characteristic of the MP-4 aberrancy, such that a disease or disorder is prevented or, alternatively, delayed in its progression. Depending on the type of MP-4 aberrancy, for example, a MP-4, MP-4 agonist or MP-4 antagonist agent can be used for treating the subject. The appropriate agent can be determined based on screening assays described herein.

2. Therapeutic Methods

Another aspect of the invention pertains to methods of modulating MP-4 expression or activity for therapeutic purposes. Accordingly, in an exemplary embodiment, the modulatory method of the invention involves contacting a cell with a MP-4 or agent that modulates one or more of the activities of MP-4 protein activity associated with the cell. An agent that modulates MP-4 protein activity can be an agent as described herein, such as a nucleic acid or a protein, a naturally-occurring target molecule of a MP-4 protein (e.g., a MP-4 substrate), a MP-4 antibody, a MP-4 agonist or antagonist, a peptidomimetic of a MP-4 agonist or antagonist, or other small molecule. In one embodiment, the agent stimulates one or more MP-4 activities. Examples of such stimulatory agents include active MP-4 protein and a nucleic acid molecule encoding MP-4 that has been introduced into the cell. In another embodiment, the agent inhibits one or more MP-4 activities. Examples of such inhibitory agents include antisense MP-4 nucleic acid molecules, anti-MP-4 antibodies, and MP-4 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a MP-4 protein or nucleic acid molecule. In one embodiment, the method involves administering an agent (e.g., an agent identified by a screening assay described herein), or combination of agents that modulates (e.g., upregulates or downregulates) MP-4 expression or activity. In another embodiment, the method involves administering a MP-4 protein or nucleic acid molecule as therapy to compensate for reduced or aberrant MP-4 expression or activity.

A preferred embodiment of the present invention involves a method for treatment of a MP-4 associated disease or disorder which includes the step of administering a therapeutically effective amount of a MP-4 antibody to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of MP-4 activity is desirable in situations in which MP-4 is abnormally downregulated and/or in which increased MP-4 activity is likely to have a beneficial effect. For example, stimulation of MP-4 activity is desirable in situations in which a MP-4 is downregulated and/or in which increased MP-4 activity is likely to have a beneficial effect. Likewise, inhibition of MP-4 activity is desirable in situations in which MP-4 is abnormally upregulated and/or in which decreased MP-4 activity is likely to have a beneficial effect.

3. Pharmacogenomics

The MP-4 molecules of the present invention, as well as agents, or modulators which have a stimulatory or inhibitory effect on MP-4 activity (e.g., MP-4 gene expression) as identified by a screening assay described herein can be administered to individuals to treat (prophylactically or therapeutically) thioredoxin active site associated disorders (e.g, a cardiovascular disorder, e.g., atherosclerosis, ischaemia reperfusion injury, cardiac hypertrophy, hypertension, coronary artery disease, myocardial infarction, arrythmia, cardiomyopathies, and congestive heart failure; a connective tissue disorder, e.g., Ehlers-Danlos Syndrome; or a hepatic disorder, e.g., alcoholic liver disease, liver cirrhosis, liver cancer) associated with aberrant MP-4 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a MP-4 molecule or MP-4 modulator as well as tailoring the dosage and/or therapeutic regimen of treatment with a MP-4 molecule or MP-4 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a MP-4 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a MP-4 molecule or MP-4 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a MP-4 molecule or MP-4 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of MP-4 cDNAs

In this example, the identification and characterization of the gene encoding human MP-4 is described.

Isolation of the human MP-4 cDNA

The invention is based, at least in part, on the discovery of a human gene encoding a novel protein, referred to herein as MP-4. The human MP-4 gene was isolated from a cDNA library which was prepared from tissue obtained from a subject suffering from congestive heart failure. Briefly, a cardiac tissue sample was obtained from a biopsy of a 42 year old woman suffering from congestive heart failure. mRNA was isolated from the cardiac tissue and a cDNA library was prepared therefrom using art known methods (described in, for example, *Molecular Cloning A Laboratory Manual,* 2nd Ed., ed. by Sambrook, Fritsch and Maniatis (Cold Spring Harbor Laboratory Press: 1989). Using a program which identifies the presence of signal peptides (Nielsen, H. et al. (1997) *Protein Engineering* 10:1–6), one positive clone was isolated.

The sequence of the entire clone was determined and found to contain a methionine-initiated open reading frame of about 280 amino acids. Signal peptide algorithms predict that MP-4 contains a signal peptide (about amino acids 7–23 of SEQ ID NO:2). The nucleotide sequence encoding the human MP-4 protein is shown in FIG. 1 and is set forth as SEQ ID NO:1. The full length protein encoded by this nucleic acid comprises about 280 amino acids and has the amino acid sequence shown in FIG. 1 and set forth as SEQ ID NO:2. The coding region (open reading frame) of SEQ ID NO:1 is set forth in SEQ ID NO:3.

Analysis of Human MP-4

A BLASTP 1.4.1 OMP-WashU search, using a score of 100 and a word length of 3 (Altschul et al. (1990) *J. Mol. Biol.* 215:403) of the amino acid sequence of human MP-4 revealed that human MP-4 shares weak similarity with *Acanthamoeba castellanii* disulfide-like protein (Accession No. L28174), *Saccharomyces cerevisiae* protein disulfide isomerase (Accession No. M62815), and a *C. elegans* protein similar to bovine protein disulphide isomerase ER-60. For example, the human MP-4 and *Acanthamoeba castellanii* disulfide-like protein share a global amino acid identity of approximately 19.2% determined using pam120.mat scoring matrix, gap penalties −12/−4, with a global alignment score of −374 (Myers and Miller (1989) CABIOS 4:11–17); and having local amino acid identity of approximately 47% identity over amino acids 45–95 of human MP-4 (about 57% identity over amino acids 45–70). Similarly, the *C. elegans* protein similar to the bovine disulphide isomerase shows a local identity approximately 51% and 60% homology over amino acids 46–86 and 113–127, respectively, of human MP-4. The percentages of local identity were estimated using the BLASTP program.

In addition, a Hidden Markov Model ("HMM") search (HMMER 2.1) of the amino acid sequence of MP-4 (SEQ ID NO:2) identified amino acids 28–126 of MP-4 as matching the HMM for thioredoxin family active site (Accession No. PF00085) with a score of 62 (E-value 2.3e-17) (FIG. 2). The *Acanthamoeba castellanii* disulfide-like protein and *Saccharomyces cerevisiae* protein disulfide isomerase also contain domains matching the HMM for thioredoxin family active site at about amino acid residues 28–133 and 161–266, and 52–140 and 375–485, respectively. The thioredoxin family active site domains present in protein disulfide isomerases constitute the active sites of protein disulfide isomerases. Importantly, the human MP-4 protein of the present invention contains the active site CXXC (amino acids 56–59 of SEQ ID NO:2) motif characteristic of thioredoxin-like protein active sites and protein disulfide isomerase protein active sites.

Human MP-4 is further predicted to contain the following sites: three transmembrane domains (TM) which extend from about amino acid 89 (extracellular end) to about amino acid 105 (cytoplasmic end) of SEQ ID NO:2; from about amino acid 137 (cytoplasmic end) to about amino acid 161 (extracellular end) of SEQ ID NO:2 and from about amino acid 182 (extracellular end) to about amino acid 206 (cytoplasmic end) of SEQ ID NO:2; six protein kinase C phosphorylation sites from amino acids 92–94, 118–120, 127–129, 208–210, 220–222, and 256–258 of SEQ ID NO:2; five casein kinase II phosphorylation sites from amino acids 68–71, 118–121, 127–130, 246–249, and 256–259 of SEQ ID NO:2; one tyrosine kinase phosphorylation site from amino acid 106–114, of SEQ ID NO:2; two N-myristoylation sites from amino acids 20–25 and 191–196 of SEQ ID NO:2; and one amidation site from amino acid 25–28 of SEQ ID NO:2.

Analysis of primary and secondary protein structure of human MP-4, as shown in FIG. 4, was performed as follows: alpha, beta turn and coil regions, Garnier-Robson algorithm (Garnier et al. (1978) *J Mol Biol* 120:97); alpha, beta, and turn regions, Chou-Fasman algorithm (Chou and Fasman (1978) *Adv in Enzymol Mol* 47:45–148); hydrophilicity and hydrophobicity plots, Kyte-Doolittle algorithm (Kyte and Doolittle (1982) *J Mol Biol* 157:105–132); alpha amphipathic and beta amphipathic regions, Eisenberg algorithm (Eisenberg et al. (1982) *Nature* 299:371–374); flexible regions, Karplus-Schulz algorithm (Karplus and Schulz (1985) *Naturwissens-Chafen* 72:212–213); antigenic index, Jameson-Wolf algorithm (Jameson and Wolf (1988) CABIOS 4:121–136); surface probability plot, Emini algorithm (Emini et al. (1985) *J Virol* 55:836–839). In the hydrophobicity plot of FIG. 3, relative hydrophobicity is shown above the dotted line, and relative hydrophilicity is shown below the dotted line.

A BLASTN 1.4.9MP-WashU search, using a score of 100 and a word length of 12 (Altschul et al. (1990) *J. Mol. Biol.* 215:403) of the nucleotide sequence of human MP-4 revealed local sequence identity in the range of 60–70% between the human MP-4 nucleotide sequence and various nucleotide sequences, including *Plasmodium falciparum* STS genomic sequences (Accession No. G37798) over nucleotides 748–807 and 768–847 of SEQ ID NO:1; *Plasmodium falciparum* glutamic acid-rich protein (Accession No. J03998) over nucleotides 748–849 of SEQ ID NO:1; and open reading frame 5' of ECRF3-G protein coupled receptor homolog over nucleotides 768–849 of SEQ ID NO:1.

Example 2

Tissue Distribution of MP-4 mRNA by Large-Scale Tissue-Specific Library Sequencing and by Northern Blot Hybridization Standard molecular biology methods (Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) were used to construct cDNA libraries in plasmid vectors from multiple human tissues. Individual cDNA clones from each library were isolated and sequenced and their nucleotide sequences were input into a database. The MP-4 nucleotide sequence of SEQ ID NO:1 was used to query the tissue-specific library cDNA clone nucleotide sequence database using the BLASTN program (Altschul S. F. et al, (1990) J. Mol. Biol. 215: 403–410.) with a word length of 12 and using the BLOSUM62 scoring matrix. Nucleotide sequences identical to portions of the MP-4 nucleotide sequence of SEQ ID NO:1 were found in cDNA libraries originating from human skin, B-cells, T-cells, spleen, kidney, lung, heart, bone, thymus, and testis. MP-4 nucleic acid sequences, fragments thereof, proteins encoded by these sequences, and fragments thereof as well as modulators of MP-4 gene or protein activity may be useful for diagnosing or treating diseases that involve the tissues in which the MP-4 mRNA is expressed.

Alternatively, Northern blot hybridizations with various RNA samples can be performed under standard conditions and washed under stringent conditions, i.e., 0.2× SSC at 65° C. A DNA probe corresponding to all or a portion of the coding region of MP-4 (SEQ ID NO:3) can be used. The DNA is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) can be probed in ExpressHyb hybridization solution (Clontech) and washed at high stringency according to manufacturer's recommendations.

Example 3

Recombinant Expression of MP-4 in Bacterial Cells

In this example, MP-4 is expressed as a recombinant glutathione-S-transferase (GST) fusion polypeptide in *E.* coli and the fusion polypeptide is isolated and characterized. Specifically, MP-4 is fused to GST and this fusion polypeptide is expressed in E. coli, e.g., strain PEB 199. As the human MP-4 protein is predicted to be approximately 54 kDa, and GST is predicted to be 26 kDa, the fusion polypeptide is predicted to be approximately 80 kDa, in molecular weight. Expression of the GST-MP-4 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant MP-4 Protein in COS Cells

To express the MP-4 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire MP-4 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the MP-4 DNA sequence is amplified by PCR using two primers. The 5' primer contains the restriction site of interest followed by approximately twenty nucleotides of the MP-4 coding sequence starting from the initiation codon; the 3' end sequence contains complementary sequences to the other restriction site of interest, a translation stop codon, the HA tag or FLAG tag and the last nucleotides of the MP-4 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the MP-4 gene is inserted in the correct orientation. The ligation mixture is transformed into E. coli cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the MP-4-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989. The expression of the MP-4 polypeptide is detected by radiolabelling ($^{35}$S-methionine or $^{35}$S-cysteine available from NEN, Boston, MA, can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the MP-4 coding sequence is cloned directly into the polylinker of the pCDNA/Amp vector using the appropriate restriction sites. The resulting plasmid is transfected into COS cells in the manner described above, and the expression of the MP-4 polypeptide is detected by radiolabelling and immunoprecipitation using a MP-4 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising the nucleotide sequence set forth in SEQ ID NO:1, or a complement thereof.

2. An isolated nucleic acid molecule comprising the nucleotide sequence set forth in SEQ ID NO:3, or a complement thereof.

3. An isolated nucleic acid molecule consisting of the nucleotide sequence set forth in SEQ ID NO:1, or a complement thereof.

4. An isolated nucleic acid molecule consisting of the nucleotide sequence set forth in SEQ ID NO:3, or a complement thereof.

5. An isolated nucleic acid molecule which encodes a polypeptide comprising the amino acid sequence set forth in SEQ ID NO:2, or a complement thereof.

6. An isolated nucleic acid molecule which encodes a polypeptide consisting of the amino acid sequence set forth in SEQ ID NO:2, or a complement thereof.

7. An isolated nucleic acid molecule comprising the nucleic acid molecule of claim 1, and a nucleotide sequence encoding a heterologous polypeptide.

8. A vector comprising the nucleic acid molecule of claim 1.

9. The vector of claim 8, which is an expression vector.

10. An isolated host cell transfected with the vector of claim 8.

11. A method of expressing a polypeptide comprising the step of culturing the isolated host cell of claim 10 under conditions in which the nucleic acid molecule is expressed, thereby expressing the polypeptide.

12. A method of producing a polypeptide comprising the step of culturing the isolated host cell of claim 10 under conditions in which the nucleic acid molecule is expressed and isolating said polypeptide from the culture medium.

13. A kit comprising the nucleic acid molecule of claim 1 and instructions for use.

14. An isolated nucleic acid molecule comprising the nucleic acid molecule of claim 2, and a nucleotide sequence encoding a heterologous polypeptide.

15. An isolated nucleic acid molecule comprising the nucleic acid molecule of claim 3, and a nucleotide sequence encoding a heterologous polypeptide.

16. An isolated nucleic acid molecule comprising the nucleic acid molecule of claim 4, and a nucleotide sequence encoding a heterologous polypeptide.

17. An isolated nucleic acid molecule comprising the nucleic acid molecule of claim 5, and a nucleotide sequence encoding a heterologous polypeptide.

18. An isolated nucleic acid molecule comprising the nucleic acid molecule of claim 6, and a nucleotide sequence encoding a heterologous polypeptide.

19. A vector comprising the nucleic acid molecule of claim 2.

20. The vector of claim 19, which is an expression vector.

21. An isolated host cell transfected with the vector of claim 19.

22. A method of expressing a polypeptide comprising die step of culturing the isolated host cell of claim 21 under conditions in which the nucleic acid molecule is expressed, thereby expressing the polypeptide.

23. A method of producing a polypeptide comprising the step of culturing the isolated host cell of claim 21 under conditions in which the nucleic acid molecule is expressed and isolating said polypeptide from the culture medium.

24. A vector comprising the nucleic acid molecule of claim 3.

25. The vector of claim 24, which is an expression vector.

26. An isolated host cell transfected with the vector of claim 24.

27. A method of expressing a polypeptide comprising the step of culturing the isolated host cell of claim 26 under conditions in which the nucleic acid molecule is expressed, thereby expressing she polypeptide.

28. A method of producing a polypeptide comprising the step of culturing the isolated host cell of claim 26 under conditions in which the nucleic acid molecule is expressed and isolating said polypeptide from the culture medium.

29. A vector comprising the nucleic acid molecule of claim 4.

30. The vector of claim 29, which is an expression vector.

31. An isolated host cell transfected with the vector of claim 29.

32. A method of expressing a polypeptide comprising the step of culturing the isolated host cell of claim 31 under conditions in which the nucleic acid molecule is expressed, thereby expressing the polypeptide.

33. A method of producing a polypeptide comprising the step of culturing the isolated host cell of claim 31 under conditions in which the nucleic acid molecule is expressed and isolating said polypeptide from the culture medium.

34. A vector comprising the nucleic acid molecule of claim 5.

35. The vector of claim 34, which is an expression vector.

36. An isolated host cell transfected with the vector of claim 34.

37. A method of expressing a polypeptide comprising the step of culturing the isolated host cell of claim 36 under conditions in which the nucleic acid molecule is expressed, thereby expressing the polypeptide.

38. A method of producing a polypeptide comprising the step of culturing the isolated host cell of claim 36 under conditions in which the nucleic acid molecule is expressed and isolating said polypeptide from the culture medium.

39. A vector comprising the nucleic acid molecule of claim 6.

40. The vector of claim 39, which is an expression vector.

41. An isolated host cell transfected with the vector of claim 39.

42. A method of expressing a polypeptide comprising the step of culturing the isolated host cell of claim 41 under conditions in which the nucleic acid molecule is expressed, thereby expressing the polypeptide.

43. A method of producing a polypeptide comprising the step of culturing the isolated host cell of claim 41 under conditions in which the nucleic acid molecule is expressed and isolating said polypeptide from the culture median.

44. A kit comprising the nucleic acid molecule of claim 2 and instructions for use.

45. A kit comprising the nucleic acid molecule of claim 3 and instructions for use.

46. A kit comprising the nucleic acid molecule of claim 4 and instructions for use.

47. A kit comprising the nucleic acid molecule of claim 5 and instructions for use.

48. A kit comprising the nucleic acid molecule of claim 6 and instructions for use.

* * * * *

SEQUENCE LISTING

```
<160> NUMBER OF SEQ ID NOS:  6

<210> SEQ ID NO 1
<211> LENGTH: 1207
<212> TYPE: DNA
<213> ORGANISM: Homo sapiens
<220> FEATURE:
<221> NAME/KEY: CDS
<222> LOCATION: (74)..(913)
<223> OTHER INFORMATION: AT POSITION 1050 N=ANY NUCLEIC ACID

<400> SEQUENCE: 1
gcccacgcgt ccgcccgcga gggcggaagt gggagctgcg accgcgctcc ctgtgaggtg        60
ggcaagcggc gaa atg gcg ccc tcc ggg agt ctt gca gtt ccc ctg gca          109
            Met Ala Pro Ser Gly Ser Leu Ala Val Pro Leu Ala
              1               5                  10 gtc ctg gtg ctg ttg ctt tgg ggt gct ccc tgg acg cac ggg cgg cgg          157
Val Leu Val Leu Leu Leu Trp Gly Ala Pro Trp Thr His Gly Arg Arg
 15                  20                  25
```

```
agc aac gtt cgc gtc atc acg gac gag aac tgg aga gaa ctg ctg gaa      205
Ser Asn Val Arg Val Ile Thr Asp Glu Asn Trp Arg Glu Leu Leu Glu
     30              35                  40 gga gac tgg atg ata gaa ttt tat gcc ccg tgg tgc cct gct tgt caa      253
Gly Asp Trp Met Ile Glu Phe Tyr Ala Pro Trp Cys Pro Ala Cys Gln
 45              50                  55                  60 aat ctt caa ccg gaa tgg gaa agt ttt gct gaa tgg gga gaa gat ctt      301
Asn Leu Gln Pro Glu Trp Glu Ser Phe Ala Glu Trp Gly Glu Asp Leu
                 65                  70                  75 gag gtt aat att gcg aaa gta gat gtc aca gag cag cca gga ctg agt      349
Glu Val Asn Ile Ala Lys Val Asp Val Thr Glu Gln Pro Gly Leu Ser
             80                  85                  90 gga cgg ttt atc ata ctg ctc ttc cta cta ttt atc tgt aaa gat ggt      397
Gly Arg Phe Ile Ile Leu Leu Phe Leu Leu Phe Ile Cys Lys Asp Gly
         95                 100                 105 gaa ttt agg cgc tat cag ggt cca agg act aag aag gac ttc ata aac      445
Glu Phe Arg Arg Tyr Gln Gly Pro Arg Thr Lys Lys Asp Phe Ile Asn
     110                 115                 120 ttt ata agt gat aaa gag tgg aag agt att gag ccc gtt tca tca tgg      493
Phe Ile Ser Asp Lys Glu Trp Lys Ser Ile Glu Pro Val Ser Ser Trp
125                 130                 135                 140 ttt ggt cca ggt tct gtt ctg atg agt agt atg tca gca ctc ttt cag      541
Phe Gly Pro Gly Ser Val Leu Met Ser Ser Met Ser Ala Leu Phe Gln
                 145                 150                 155 cta tct atg tgg atc agg acg tgc cat aac tac ttt att gaa gac ctt      589
Leu Ser Met Trp Ile Arg Thr Cys His Asn Tyr Phe Ile Glu Asp Leu
             160                 165                 170 gga ttg cca gtg tgg gga tca tat act gtt ttt gct tta gca act ctg      637
Gly Leu Pro Val Trp Gly Ser Tyr Thr Val Phe Ala Leu Ala Thr Leu
         175                 180                 185 ttt tcc gga ctg tta tta gga ctc tgt atg ata ttt gtg gca gat tgc      685
Phe Ser Gly Leu Leu Leu Gly Leu Cys Met Ile Phe Val Ala Asp Cys
     190                 195                 200 ctt tgt cct tca aaa agg cgc aga cca cag cca tac cca tac cct tca      733
Leu Cys Pro Ser Lys Arg Arg Arg Pro Gln Pro Tyr Pro Tyr Pro Ser
205                 210                 215                 220 aaa aaa tta tta tca gaa tct gca caa cct ttg aaa aaa gtg gag gag      781
Lys Lys Leu Leu Ser Glu Ser Ala Gln Pro Leu Lys Lys Val Glu Glu
                 225                 230                 235 gaa caa gag gcg gat gaa gaa gat gtt tca gaa gaa gaa gct gaa agt      829
Glu Gln Glu Ala Asp Glu Glu Asp Val Ser Glu Glu Glu Ala Glu Ser
             240                 245                 250 aaa gaa gga aca aac aaa gac ttt cca cag aat gcc ata aga caa cgc      877
Lys Glu Gly Thr Asn Lys Asp Phe Pro Gln Asn Ala Ile Arg Gln Arg
         255                 260                 265 tct ctg ggt cca tca ttg gcc cag ata aat cct agt taaattttat          923
Ser Leu Gly Pro Ser Leu Ala Gln Ile Asn Pro Ser
     270                 275                 280 agttatctta atattatgat tttgataaaa acagaagatt gatcattttg tttggtttga    983
agtgaactgg acttttttga atattgcagg gttcagtcta gattgtcatt aaattgaaga   1043
gtctacnttc agaacataaa agcactaggt atacaagttt gaaatatgat ttaagcacag   1103
tatgatggtt taaatagttc tctaattttt gaaaaatcgt gccaagcaat aagatttatg   1163
tatatttgtt taataataac ctatttcaag tctgagtttt gaaa                    1207

<210> SEQ ID NO 2
<211> LENGTH: 280
<212> TYPE: PRT
```

<213> ORGANISM: Homo sapiens

<400> SEQUENCE: 2

```
Met Ala Pro Ser Gly Ser Leu Ala Val Pro Leu Ala Val Leu Val Leu
 1               5                  10                  15

Leu Leu Trp Gly Ala Pro Trp Thr His Gly Arg Arg Ser Asn Val Arg
             20                  25                  30

Val Ile Thr Asp Glu Asn Trp Arg Glu Leu Leu Glu Gly Asp Trp Met
         35                  40                  45

Ile Glu Phe Tyr Ala Pro Trp Cys Pro Ala Cys Gln Asn Leu Gln Pro
     50                  55                  60

Glu Trp Glu Ser Phe Ala Glu Trp Gly Glu Asp Leu Glu Val Asn Ile
 65                  70                  75                  80

Ala Lys Val Asp Val Thr Glu Gln Pro Gly Leu Ser Gly Arg Phe Ile
                 85                  90                  95

Ile Leu Leu Phe Leu Leu Phe Ile Cys Lys Asp Gly Glu Phe Arg Arg
            100                 105                 110

Tyr Gln Gly Pro Arg Thr Lys Lys Asp Phe Ile Asn Phe Ile Ser Asp
        115                 120                 125

Lys Glu Trp Lys Ser Ile Glu Pro Val Ser Ser Trp Phe Gly Pro Gly
130                 135                 140

Ser Val Leu Met Ser Ser Met Ser Ala Leu Phe Gln Leu Ser Met Trp
145                 150                 155                 160

Ile Arg Thr Cys His Asn Tyr Phe Ile Glu Asp Leu Gly Leu Pro Val
                165                 170                 175

Trp Gly Ser Tyr Thr Val Phe Ala Leu Ala Thr Leu Phe Ser Gly Leu
            180                 185                 190

Leu Leu Gly Leu Cys Met Ile Phe Val Ala Asp Cys Leu Cys Pro Ser
        195                 200                 205

Lys Arg Arg Arg Pro Gln Pro Tyr Pro Tyr Pro Ser Lys Lys Leu Leu
    210                 215                 220

Ser Glu Ser Ala Gln Pro Leu Lys Lys Val Glu Glu Gln Glu Ala
225                 230                 235                 240

Asp Glu Glu Asp Val Ser Glu Glu Ala Glu Ser Lys Glu Gly Thr
                245                 250                 255

Asn Lys Asp Phe Pro Gln Asn Ala Ile Arg Gln Arg Ser Leu Gly Pro
            260                 265                 270

Ser Leu Ala Gln Ile Asn Pro Ser
        275                 280
```

<210> SEQ ID NO 3
<211> LENGTH: 840
<212> TYPE: DNA
<213> ORGANISM: Homo sapiens
<220> FEATURE:
<221> NAME/KEY: CDS
<222> LOCATION: (1)..(840)

<400> SEQUENCE: 3

```
atg gcg ccc tcc ggg agt ctt gca gtt ccc ctg gca gtc ctg gtg ctg      48
Met Ala Pro Ser Gly Ser Leu Ala Val Pro Leu Ala Val Leu Val Leu
 1               5                  10                  15 ttg ctt tgg ggt gct ccc tgg acg cac ggg cgg cgg agc aac gtt cgc      96
Leu Leu Trp Gly Ala Pro Trp Thr His Gly Arg Arg Ser Asn Val Arg
             20                  25                  30 gtc atc acg gac gag aac tgg aga gaa ctg ctg gaa gga gac tgg atg     144
Val Ile Thr Asp Glu Asn Trp Arg Glu Leu Leu Glu Gly Asp Trp Met
         35                  40                  45
```

```
                  35                  40                  45
ata gaa ttt tat gcc ccg tgg tgc cct gct tgt caa aat ctt caa ccg     192
Ile Glu Phe Tyr Ala Pro Trp Cys Pro Ala Cys Gln Asn Leu Gln Pro
         50                  55                  60 gaa tgg gaa agt ttt gct gaa tgg gga gaa gat ctt gag gtt aat att     240
Glu Trp Glu Ser Phe Ala Glu Trp Gly Glu Asp Leu Glu Val Asn Ile
 65                  70                  75                  80 gcg aaa gta gat gtc aca gag cag cca gga ctg agt gga cgg ttt atc     288
Ala Lys Val Asp Val Thr Glu Gln Pro Gly Leu Ser Gly Arg Phe Ile
                 85                  90                  95 ata ctg ctc ttc cta cta ttt atc tgt aaa gat ggt gaa ttt agg cgc     336
Ile Leu Leu Phe Leu Leu Phe Ile Cys Lys Asp Gly Glu Phe Arg Arg
            100                 105                 110 tat cag ggt cca agg act aag aag gac ttc ata aac ttt ata agt gat     384
Tyr Gln Gly Pro Arg Thr Lys Lys Asp Phe Ile Asn Phe Ile Ser Asp
        115                 120                 125 aaa gag tgg aag agt att gag ccc gtt tca tca tgg ttt ggt cca ggt     432
Lys Glu Trp Lys Ser Ile Glu Pro Val Ser Ser Trp Phe Gly Pro Gly
130                 135                 140 tct gtt ctg atg agt agt atg tca gca ctc ttt cag cta tct atg tgg     480
Ser Val Leu Met Ser Ser Met Ser Ala Leu Phe Gln Leu Ser Met Trp
145                 150                 155                 160 atc agg acg tgc cat aac tac ttt att gaa gac ctt gga ttg cca gtg     528
Ile Arg Thr Cys His Asn Tyr Phe Ile Glu Asp Leu Gly Leu Pro Val
                165                 170                 175 tgg gga tca tat act gtt ttt gct tta gca act ctg ttt tcc gga ctg     576
Trp Gly Ser Tyr Thr Val Phe Ala Leu Ala Thr Leu Phe Ser Gly Leu
            180                 185                 190 tta tta gga ctc tgt atg ata ttt gtg gca gat tgc ctt tgt cct tca     624
Leu Leu Gly Leu Cys Met Ile Phe Val Ala Asp Cys Leu Cys Pro Ser
        195                 200                 205 aaa agg cgc aga cca cag cca tac cca tac cct tca aaa aaa tta tta     672
Lys Arg Arg Arg Pro Gln Pro Tyr Pro Tyr Pro Ser Lys Lys Leu Leu
210                 215                 220 tca gaa tct gca caa cct ttg aaa aaa gtg gag gag gaa caa gag gcg     720
Ser Glu Ser Ala Gln Pro Leu Lys Lys Val Glu Glu Glu Gln Glu Ala
225                 230                 235                 240 gat gaa gaa gat gtt tca gaa gaa gaa gct gaa agt aaa gaa gga aca     768
Asp Glu Glu Asp Val Ser Glu Glu Glu Ala Glu Ser Lys Glu Gly Thr
                245                 250                 255 aac aaa gac ttt cca cag aat gcc ata aga caa cgc tct ctg ggt cca     816
Asn Lys Asp Phe Pro Gln Asn Ala Ile Arg Gln Arg Ser Leu Gly Pro
            260                 265                 270 tca ttg gcc cag ata aat cct agt                                     840
Ser Leu Ala Gln Ile Asn Pro Ser
        275                 280

<210> SEQ ID NO 4
<211> LENGTH: 21
<212> TYPE: DNA
<213> ORGANISM: Homo sapiens

<400> SEQUENCE: 4
gcgccatttc gccgcttgcc c                                              21

<210> SEQ ID NO 5
<211> LENGTH: 31
<212> TYPE: DNA
<213> ORGANISM: Homo sapiens

<400> SEQUENCE: 5
```

-continued

```
ggagggcgcc atttcgccgc ttgcccacct c                           31
```

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: consensus
      sequence

<400> SEQUENCE: 6

```
Ser Ser Val Val Val Leu Thr Asp Glu Asn Phe Asp Glu Glu Val
 1               5                  10                  15

Leu Lys Ala Lys Ser Asp Lys Pro Val Leu Val Asp Phe Tyr Ala Pro
            20                  25                  30

Trp Cys Gly Pro Cys Lys Met Leu Ala Pro Glu Tyr Glu Lys Leu Ala
            35                  40                  45

Gln Glu Tyr Lys Gly Glu Ser Asp Asp Val Lys Phe Ala Lys Val Asp
        50                  55                  60

Ala Asp Glu Asn Pro Lys Asp Leu Ala Ser Lys Tyr Gly Val Arg Gly
65                  70                  75                  80

Phe Pro Thr Leu Lys Phe Phe Lys Asn Gly Lys Lys Glu Pro Val Asp
                85                  90                  95

Tyr Val Gly Gly Ala Arg Thr Lys Asp Asp Leu Val Ala Phe Ile
               100                 105                 110
```